United States Patent
Beckett et al.

[11] Patent Number: 6,022,873
[45] Date of Patent: Feb. 8, 2000

[54] METALLOPROTEINASE INHIBITORS

[75] Inventors: Raymond Paul Beckett; Fionna Mitchell Martin; Andrew Miller; Richard Simon Todd; Mark Whittaker, all of Oxford, United Kingdom

[73] Assignee: British Biotech Pharmaceuticals Limited, United Kingdom

[21] Appl. No.: 09/121,033

[22] Filed: Jul. 23, 1998

Related U.S. Application Data

[63] Continuation-in-part of application No. PCT/GB97/02891, Oct. 20, 1997.

[30] Foreign Application Priority Data

Oct. 19, 1996 [GB] United Kingdom ............... 9621814

[51] Int. Cl.[7] .................. A61K 31/47; A61K 31/445; A61K 31/535; C07D 295/18; C07D 401/12
[52] U.S. Cl. ............. 514/237.5; 514/212; 514/227.5; 514/227.8; 514/252; 514/255; 514/307; 514/314; 514/319; 514/330; 514/423; 540/450; 540/467; 540/470; 540/544; 540/555; 540/596; 544/160; 544/383; 544/59; 544/238; 544/359; 544/387; 546/148; 546/172; 546/206; 546/208; 546/211; 546/226; 548/530; 548/540
[58] Field of Search .................. 546/226, 206, 546/172, 148; 544/160, 383; 514/330, 319, 314, 237.5, 255, 307

[56] References Cited

U.S. PATENT DOCUMENTS 5,614,625 3/1997 Broadhurst .................. 540/480

FOREIGN PATENT DOCUMENTS

| 2 007 663 | 5/1979 | United Kingdom . |
|---|---|---|
| 93/14066 | 7/1993 | WIPO . |
| 94/18185 | 8/1994 | WIPO . |
| 96/27583 | 9/1996 | WIPO . |
| 97/25315 | 7/1997 | WIPO . |
| 98/17655 | 4/1998 | WIPO . |

OTHER PUBLICATIONS

Brown FK et. al. J. Med. Chem. 37, 674–688, 1994.

*Primary Examiner*—Evelyn Mei Huang
*Attorney, Agent, or Firm*—Banner & Witcoff, Ltd.

[57] ABSTRACT

Compounds of formula (I)

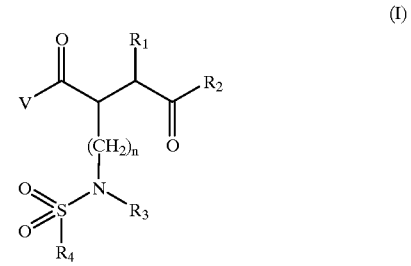

wherein n, V, $R_1$, $R_2$, $R_3$ and $R_4$ are as defined in the specification are matrix metalloproteinase inhibitors.

22 Claims, No Drawings

METALLOPROTEINASE INHIBITORS

This is a continuation-in-part application of International Application PCT/GB97/02891, with an international filing date of Oct. 20, 1997, which is based on Great Britain Application No. 9621814.4 filed Oct. 19, 1996.

The present invention relates to therapeutically active hydroxamic and carboxylic acid derivatives, to processes for their preparation, to pharmaceutical compositions containing them, and to the use of such compounds in medicine. In particular, the compounds are inhibitors of matrix metalloproteinases involved in tissue degradation, especially collagenases such as human fibroblast collagenase (MMP-1), human neutrophil collagenase (MMP-8) and collagenase-3 (MMP-13).

BACKGROUND TO THE INVENTION

Compounds which have the property of inhibiting the action of metalloproteinases involved in connective tissue breakdown such as collagenases, stromelysins and/or gelatinases (known as "matrix metalloproteinases", and herein referred to as MMPs) are thought to be potentially useful for the treatment or prophylaxis of conditions involving such tissue breakdown, for example rheumatoid arthritis, osteoarthritis, osteopenias such as osteoporosis, periodontitis, gingivitis, corneal epidermal or gastric ulceration, and tumour metastasis, invasion and growth. MMP inhibitors are also of potential value in the treatment of neuroinflammatory disorders, including those involving myelin degradation, for example multiple sclerosis, as well as in the management of angiogenesis dependent diseases, which include arthritic conditions and solid tumour growth as well as psoriasis, proliferative retinopathies, neovascular glaucoma, ocular tumours, angiofibromas and hemangiomas. However, the relative contributions of individual MMPs in any of the above disease states is not yet fully understood.

Metalloproteinases are characterised by the presence in the structure of a zinc(II) ionic site. It is now known that there exists a range of metalloproteinase enzymes that includes human fibroblast collagenase (MMP-1), human neutrophil collagenase (MMP-8) and collagenase-3 (MMP-13), 72 kDa-gelatinase, 92 kDa-gelatinase, stromelysin-1, stromelysin-2 and PUMP-1 (J. F. Woessner, FASEB J, 1991, 5, 2145–2154).

Known classes of collagenase inhibitors include those disclosed in EP-A-0574758 (Roche), EP-A-0684240 (Roche), and WO 95/33731 (Roche). In general, the compounds disclosed in those publications may be represented by the structural formula (IA)

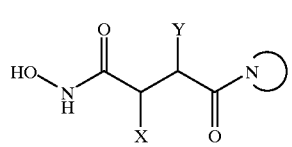

(IA)

in which X, Y and the N-containing ring are variable in accordance with the specific disclosures of the publications.

BRIEF DESCRIPTION OF THE INVENTION

This invention makes available a novel class of compounds which are inhibitors of matrix metalloproteinases. In general, they are selective inhibitors of collagenases, such as human fibroblast collagenase, over gelatinases, stromelysins and matrilysin, and are therefore indicated for treatment of diseases primarily mediated by collagenases. The class includes compounds which are capable of being administered orally, as indicated by oral dosing tests in laboratory animals.

The compounds of the invention conform to general formula (IA), but differ in structure from prior art compounds of that general formula principally in the identity of the group X. In the compounds of the present invention, the group X is a sulfonamidoalkyl group, not contemplated by any of EP-A-0574758, EP-A-0684240, or WO 95/33731.

DETAILED DESCRIPTION OF THE INVENTION

According to the present invention there is provided a compound of formula (I)

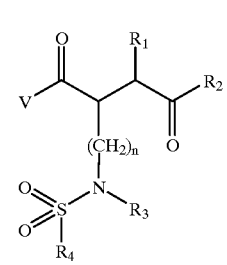

(I)

wherein
V is HO— or HONH—
n is 1, 2, 3 or 4;
$R_1$ is a $C_1$–$C_{12}$ alkyl,
$C_2$–$C_{12}$ akenyl,
$C_2$–$C_{12}$ alkynyl,
perfluoroalkyl,
phenyl($C_{1-C6}$ alkyl)-,
heteroaryl($C_{1-C6}$ alkyl)-,
non-aryl heterocyclyl($C_1$–$C_6$ alkyl)-,
cycloalkyl($C_1$–$C_6$ alkyl)-,
cycloalkenyl($C_1$–$C_6$ alkyl)-,
phenoxy($C_1$–$C_6$ alkyl)-,
heteroaryloxy($C_1$–$C_6$ alkyl)-,
phenyl($C_1$–$C_6$ alkyl)O($C_1$–$C_6$ alkyl)-,
heteroaryl($C_1$–$C_6$ alkyl)O($C_1$–$C_6$ alkyl)-,
phenyl($C_1$–$C_6$ alkyl)S($C_{1-6}$ alkyl)- or
heteroaryl($C_1$–$C_6$ alkyl)S($C_{1-6}$ alkyl)- group,
any one of which may be optionally substituted by $C_1$–$C_6$ alkyl, trifluoromethyl, $C_1$–$C_6$ alkoxy, hydroxy, halo, cyano (—CN), phenyl, substituted phenyl or heteroaryl;
$R_2$ is a saturated 5- to 8-membered monocyclic or bridged N-heterocyclic ring which is attached via the N atom and which, when it is monocyclic, (i) optionally contains as a ring member O, S, SO, $SO_2$, or $NR_5$ wherein $R_5$ is hydrogen, hydroxy, $C_1$–$C_6$ alkyl, ($C_1$–$C_6$ alkoxy) $C_{1-6}$ alkyl, benzyl, acyl, an amino protecting group, or a group —$SO_2R_6$ wherein $R_6$ is $C_1$–$C_6$ alkyl or a substituted or unsubstituted phenyl or heteroaryl group, and/or (ii) is optionally substituted on one or more C atoms by hydroxy, $C_1$–$C_6$ alkyl, $C_1$–$C_6$ alkoxy, cyano, oxo, ketalised oxo, amino, mono($C_1$–$C_6$ alkyl)amino, di($C_1$–$C_6$ alkyl)amino, carboxy, $C_1$–$C_6$ alkoxycarbonyl, hydroxymethyl, $C_1$–$C_6$ alkoxymethyl, carbamoyl, mono($C_1$–$C_6$ alkyl)carbamoyl, di($C_1$–$C_6$ alkyl)carbamoyl, or hydroxyimino;

$R_3$ is hydrogen, $C_1$–$C_6$ alkyl, benzyl, acyl, an amino protecting group, or a group —$(CH_2)_m COZ$ where m is an integer from 1 to 6, and Z represents OH, $C_1$–$C_6$ alkoxy or —$NR_x R_y$ where $R_x$, $R_y$ each independently represent hydrogen or $C_1$–$C_6$ alkyl; and $R_4$ is optionally substituted
- $C_1$–$C_6$ alkyl,
- $C_2$–$C_6$ alkenyl,
- $C_2$–$C_6$ alkynyl,
- $C_1$–$C_3$ perfluoroalkyl,
- cycloalkyl,
- cycloalkyl($C_1$–$C_6$ alkyl)-,
- cycloalkenyl,
- cycloalkenyl($C_1$–$C_6$ alkyl)-,
- di-($C_1$–$C_6$ alkyl)amino,
- phenyl,
- phenyl($C_1$–$C_6$ alkyl)-,
- biphenyl,
- phenyl-heteroaryl,
- naphthyl,
- non-aryl heterocyclyl,
- non-aryl heterocyclyl($C_1$–$C_6$ alkyl)-,
- heteroaryl or
- heteroaryl($C_1$–$C_6$ alkyl)-;
- heteroaryl-phenyl;
- heteroaryl-heteroaryl;
- aryloxyaryl or $R_3$ and $R_4$ taken together represent a divalent $C_3$–$C_6$ alkylene or alkenylene group which may optionally be (i) substituted by an oxo group, and/or (ii) substituted by ($C_1$–$C_6$)alkoxy, hydroxy, mercapto, ($C_1$–$C_6$) alkylthio, amino, halo (including fluoro, chloro, bromo and iodo), cyano, trifluoromethyl, nitro, —COOH, —$CONH_2$, —$CONHR^A$ or —$CONR^A R^B$ wherein $R^A$ and $R^B$ are independently a ($C_1$–$C_6$)alkyl group, and/or (iii) fused to a phenyl or heteroaryl group which itself may be substituted;

and pharmaceutically acceptable salts hydrates and solvates thereof.

The term "cycloalkyl" as used herein means a saturated alicyclic ring having from 3–8 carbon atoms and includes, for example, cyclopropyl, cyclobutyl, cyclopentyl, cyclohexyl, cycloheptyl and cyclooctyl.

The term "cycloalkenyl" as used herein means an unsaturated alicyclic ring having from 5–8 carbon atoms and includes, for example, cyclopentenyl, cyclohexenyl, cycloheptenyl and cyclooctenyl. The ring may contain more than one double bond.

The term "acyl" as used herein means a group RC(=O)— wherein R is $C_1$–$C_6$ alkyl or substituted $C_{1-6}$ alkyl, phenyl or substituted phenyl, phenyl($C_{1-6}$ alkyl)- or substituted phenyl($C_1$–$C_6$ alkyl)-.

The term "non-aryl heterocyclyl" means a 5–7 membered heterocyclic ring containing one, two or three heteroatoms selected from S, N and O in which at least two adjoining atoms are saturated. Examples include morpholinyl, thiomorpholinyl, dihydrofuranyl, tetrahydrothienyl, dihydrothienyl, piperidinyl, pyrrolidinyl, pyrrolinyl, dioxolanyl, oxathiolanyl, imidazolinyl, imidazolidinyl, pyrazolinyl, pyrazolidinyl, pyranyl, dioxanyl, dithianyl, oxathianyl, and piperazinyl.

The term "heteroaryl" means a 5–7 membered aromatic heterocyclic ring containing one or more heteroatoms selected from S, N and O, and optionally fused to a benzene ring. Illustrative of such rings are thienyl, furyl, pyrrolyl, imidazolyl, benzimidazolyl, thiazolyl, pyrazolyl, isoxazolyl, isothiazolyl, triazolyl, thiadiazolyl, oxadiazolyl, pyridinyl, pyridazinyl, pyrimidinyl, pyrazinyl and triazinyl.

Unless otherwise specified in the context in which it occurs, the term "substituted" as applied to any moiety herein means substituted with up to four substituents, each of which independently may be $C_1$–$C_6$ alkyl, ($C_1$–$C_6$) alkoxy, hydroxy, mercapto, ($C_{1-C_6}$)alkylthio, amino, halo (including fluoro, chloro, bromo and iodo), cyano, trifluoromethyl, nitro, —COOH, —$CONH_2$, —$CONHR^A$ or —$CONR^A R^B$ wherein $R^A$ and $R^B$ are indendently a ($C_1$–$C_6$) alkyl group or the residue of a natural alpha-amino acid, or substituted with a phenyl group which itself may be substituted by any of the foregoing.

Salts of the compounds of the invention include physiologically acceptable acid addition salts for example hydrochlorides, hydrobromides, sulfates, methane sulfonates, p-toluenesulfonates, phosphates, acetates, citrates, succinates, lactates, tartrates, fumarates and maleates. Salts may also be formed with bases, for example sodium, potassium, magnesium, and calcium salts.

There are at least two chiral centres in the compounds according to the invention because of the presence of asymmetric carbon atoms. The presence of these asymmetric carbon atoms gives rise to a number of diastereomers with R or S stereochemistry at each chiral centre. General formula (I), and (unless specified otherwise) all other formulae in this specification are to be understood to include all such stereoisomers and mixtures (for example racemic mixtures) thereof.

In the compounds of the invention, the preferred stereochemistry is in general as follows:

C atom carrying the $R_1$ group-R

C atom carrying the —(C=O)V group-S, but mixtures in which the above configurations predominate are also contemplated.

As mentioned above, the compounds of the present invention differ in structure from the collagenase inhibitors disclosed in EP-A-0574758, EP-A-0684240, or WO 95/33731 principally in that they have the above defined $R_4$—($SO_2$)—$N(R_3)$—($CH_2$)— group on the carbon atom carrying the hydroxamic acid group. Accordingly the groups $R_1$ and $R_2$ of the compounds of this invention may include those which have been disclosed in the corresponding positions of compounds disclosed in any of EP-A-0574758, EP-A-0684240, or WO 95/33731. Without limiting the generality of the foregoing, examples of substituents $R_1$ and $R_2$ are given below.

In the compounds of the invention:

n may be 1, 2 or 3. Compounds wherein n is 1 are at present preferred for their activity as collagenase selective inhibitors;

V is preferably HONH—;

$R_1$ may for example be optionally substituted $C_1$–$C_{12}$ alkyl or $C_3$–$C_6$ alkenyl; cycloalkyl($C_1$–$C_6$ alkyl); or phenyl($C_1$–$C_6$ alkyl)- or phenoxy($C_1$–$C_6$ alkyl), either of which may be optionally substituted in the phenyl ring by halogen, $C_1$–$C_6$ alkyl, $C_1$–$C_6$ alkoxy or phenyl. Specific examples of such groups include n-propyl, isopropyl, n-butyl, iso-butyl, n-pentyl, n-hexyl, n-heptyl, n-octyl, n-nonyl, n-decyl, cyclopropylmethyl, cyclobutylmethyl, cyclopentylmethyl, cyclohexylmethyl, cyclobutylethyl, 1,1,1-trifluoropropyl, phenylpropyl, 4-chlorophenylpropyl, 4-methylphenylpropyl, 4-methoxyphenylpropyl, 4-phenylphenylpropyl, 4-(4-chlorophenyl)phenylpropyl and phenoxybutyl. In compounds which have activity as collagenase selective inhibitors $R_1$ is preferably $C_1$–$C_{12}$ alkyl or fluoro-substituted alkyl, for example $C_1$–$C_6$ alkyl such as iso-butyl, or cycloalkyl ($C_1$–$C_6$ alkyl) such cyclopentylmethyl $R_2$ may for example be substituted or unsubstituted 1-pyrrolidinyl, piperidino, 1-piperazinyl, hexahydro-1-pyridazinyl, morpholino, tetrahydro-1,4-thiazin-4-yl, tetrahydro-1,4-thiazin-4-yl 1-oxide, tetrahydro-1,4-thiazin-4-yl 1,1-dioxide, thiazolidin-3-yl, hexahydroazipino, or octahydroazocino. Specific examples of such groups include piperidin-1-yl, 2-(methylcarbamoyl)-1-pyrrolidinyl, 2-(hydroxymethyl)-1-pyrrolidinyl, 4-hydroxypiperidino, 2-(methylcarbamoyl)piperidino, 4-hydroxyiminopiperidino, 4-methoxypiperidino, 4-methyl-1-piperazinyl, 4-phenyl-1-piperazinyl, 1,4-dioxa-8-azaspiro[4,5]decan-8-yl, hexahydro-3-(methylcarbamoyl)-2-pyridazinyl, hexahydro-1-(benzyloxycarbonyl)-2-pyridazinyl, 5,5-dimethyl-4-methylcarbamoyl-thiazolidin-3-yl, or 5,5-dimethyl-4-propylcarbamoyl-thiazolidin-3-yl. In compounds which have activity as collagenase selective inhibitors, $R_2$ is preferably piperidin-1-yl.

$R_3$ may for example be hydrogen, methyl, ethyl, n- or iso-propyl, n-, sec- or tert-butyl, n-pentyl, n-hexyl, benzyl, or acetyl. In compounds which have activity as collagenase selective inhibitors $R_3$ is preferably hydrogen, acetyl or methyl.

$R_4$ may for example be substituted or unsubstituted methyl, ethyl, n- or iso-propyl, n-, sec- or tert-butyl, n-pentyl, n-hexyl, n-heptyl, n-octyl, cyclopropyl, cyclobutyl, cyclopentyl, cyclohexyl, cycloheptyl, cyclooctyl, cyclopentenyl, cyclohexenyl, cycloheptenyl, cyclooctenyl, phenyl, biphenyl, naphth-1-yl, naphth-2-yl, benzyl, thien-2-yl, furan-2-yl, pyrrolyl, imidazol-2-yl, benzimidazolyl, thiazol-2-yl, benzothiazol-2-yl, pyrazolyl, isoxazol-5-yl, isothiazolyl, triazolyl, thiadiazol-5-yl, oxadiazol-5-yl, pyridin-2-yl, pyridin-3-yl, pyridin-4-yl, N-oxides of pyridin-2-yl, pyridin-3-yl and pyridin-4-yl, quinolinyl, 1,2-pyridazin-3-yl, 1,3-pyrimidin-5-yl, pyrazin-2-yl, triazinyl, piperazin-1-yl, indol-2-yl, benzimidazol-2-yl, benzotriazol-2-yl, 1,3-dithian-2-yl, and benzo[b]thien-2-yl, or quinolin-3-yl.

Specific examples of substituted $R_4$ groups include, 2-methoxyphenyl, 3-methoxyphenyl, 4-methoxyphenyl, 4-(n-butoxy)phenyl, 3,4-dimethoxyphenyl, 2,5-dimethoxyphenyl, 2-fluorophenyl, 3-fluorophenyl, 4-fluorophenyl, 2-chlorophenyl, 3-chlorophenyl, 4-chlorophenyl, 3,4-dichlorophenyl, 3,5-dichlorophenyl, 2-chloro-5-trifluoromethyphenyl, 2-bromophenyl, 3-bromophenyl, 4-bromophenyl, 2-iodophenyl, 3-iodophenyl, 4-iodophenyl, 2-methylphenyl, 3-methylphenyl, 4-methylphenyl, 3,4-dimethyl, 2,5-dimethyl-4-chlorophenyl, 2-methoxy-5-chlorophenyl, 2-t-butylphenyl, 3-t-butylphenyl, 4-t-butylphenyl, 4-t-butyl-2,6-dimethylphenyl, 4-(1,1-dimethylpropyl)phenyl, 4-phenylphenyl, 4-(4-chlorophenyl)phenyl, 4-(pyridin-4-yl)phenyl, 2-nitrophenyl, 3-nitrophenyl, 4-nitrophenyl, 2-cyanophenyl, 3-cyanophenyl, 4-cyanophenyl, 2-acetylphenyl, 3-acetylphenyl, 4-acetylphenyl, 2-methylsulfonylphenyl, 3-methylsulfonylphenyl, 4-methylsulfonylphenyl, 2-trifluoromethylphenyl, 3-trifluoromethylphenyl, 4-trifluoromethylphenyl, 3,5-ditrifluoromethylphenyl, 2-aminophenyl, 3-aminophenyl, 4-aminophenyl, 2-N,N-dimethylaminophenyl, 3-N,N-dimethylaminophenyl, 4-N,N-dimethylaminophenyl, 2-hydroxyphenyl, 3-hydroxyphenyl, 4-hydroxyphenyl, 6-dimethylaminonaphth-1-yl; $N^1$-methyl-3-methyl-5-chloroimidazol-4-yl, 4-ethoxycarbonylmethyl-thiazol-2-yl, 4-phenylthiazol-2-yl, 4,5-dimethylthiazol-2-yl, 5-bromothiazol-2-yl, 4-tert-butylthiazol-2-yl, 1,2,4-oxadiazol-5-yl, 3-methyl-1,2,4-oxadiazol-5-yl, 3-phenyl-1,2,4-oxadiazol-5-yl, 1,2,4-oxadiazol-3-yl, 1,3,4-oxadiazol-2-yl, 1,2,4-thiadiazol-5-yl, 3-phenyl-1,2,4-thiadiazol-5-yl, 1,3,4-thiadiazol-2-yl, and 5-methyl-1,3,4-thiadiazol-2-yl.

Presently preferred are compounds in which $R_4$ is methyl, ethyl, n-butyl, n-octyl, dimethylamino, trifluoromethyl, phenyl, 4-methoxyphenyl, 4-butoxyphenyl, 2,5-dimethoxyphenyl, 4-chlorophenyl, 3,4-dichlorophenyl, 2-chloro-5-methoxyphenyl, 2-chloro-5-trifluoromethylphenyl, 5-chloro-1,3-dimethyl-phenyl-5-chloro-1,3-dimethyl-1H-pyrazol-4-yl, naphth-1-yl, naphth-2-yl, 5-dimethylaminonaphth-1-yl, or thien-2-yl, 4-methylphenylmethyl, 4-(1,1-dimethylpropyl)phenyl, 4-biphenyl, quinolin-8-yl.

$R_3$ and $R_4$ taken together with the N and S atoms to which they are attached may represent a group of formula (II) or (III)

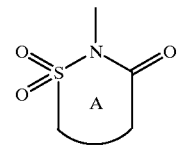

(II)

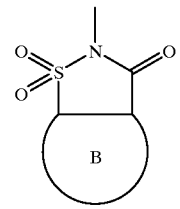

(III)

wherein ring A is a substituted or unsubstituted, saturated or unsaturated 5–8 membered ring and ring B is a substituted or unsubstituted fused phenyl or heteroaryl (e.g. thienyl or pyridinyl) ring.

Specific compounds of the invention include those prepared according to the Examples below, and pharmaceutically acceptable salts, hydrates and solvates thereof. Compounds which are particularly interesting include:

2S-{[(4-Methoxybenzenesulfonyl)-methyl-amino]-methyl}-5-methyl-3R-(piperidine-1-carbonyl)-hexanoic acid hydroxyamide, 5-Methyl-2S-{[methyl-(toluene-4-sulfonyl)-amino]-methyl]-3R-(piperidine-1-carbonyl)-hexanoic acid hydroxyamide, 2S-{[(5-Dimethylamino-naphthalene-1-sulfonyl)-methyl-amino]-methyl}-5-methyl-3R-(piperidine-1-carbonyl)-hexanoic acid hydroxyamide, 5-Methyl-2S-{[methyl-(naphthalene-2-sulfonyl)-amino]-methyl}-3R-(piperidine-1-carbonyl)-hexanoic acid hydroxyamide, 5-Methyl-2S-[(methyl-phenylmethanesulfonyl-amino)-methyl]-3R-(piperidine-1-carbonyl)-hexanoic acid hydroxyamide, 2S-{[(4-Butoxybenzenesulfonyl)-methyl-amino]-methyl}-5-methyl-3R-(piperidine-1-carbonyl)-hexanoic acid hydroxyamide, 2S-{[(Biphenyl-4-sulfonyl)-methyl-amino}-methyl}-5-methyl-3R-(piperidine-1-carbonyl)-hexanoic acid hydroxyamide, and pharmaceutically acceptable salts, hydrates and solvates thereof Additional compounds of the invention are the following:

2S-{[(5-Dimethylaminonaphthalene-1-sulfonyl)-methyl-amino]-methyl}-5-methyl-3R-(morpholine-4-carbonyl)-hexanoic acid hydroxyamide 3R-Cyclopentylmethyl-N-hydroxy-2S-[(methanesulfonyl-methyl-amino)-methyl)]-4-oxo-4-piperidin-1-yl-butyramide 3R-Cyclopentylmethyl-N-hydroxy-2S-[(methanesulfonyl-methyl-amino)-methyl)]-4-morpholin-4-yl-4-oxo-butyramide 3R-Cyclopentylmethyl-N-hydroxy-2S-{[(4-benzenesulfonyl)-methyl-amino]-methyl}-4-oxo-4-piperidine-1-yl-butyramide 3R-Cyclopentylmethyl-N-hydroxy-2S-{[(4-benzenesulfonyl)-methyl-amino]-methyl}-4-morpholin-4-yl-4-oxo-butyramide 2S-[(Methanesulfonyl-methyl-amino)-methyl]-5-methyl-3R-(morpholine-4-carbonyl)-hexanoic acid hydroxyamide 2S-{[Ethyl-(4-methoxy-benzenesulfonyl)-amino]-methyl}-5-methyl-3R-(morpholine-4-carbonyl)-hexanoic acid hydroxyamide 2S-{[Ethyl-(4-methoxy-benzenesulfonyl)-amino]-methyl}-5-methyl-3R-(piperidine-1-carbonyl)-hexanoic acid hydroxyamide 3R-Cyclopentylmethyl-2S-{[ethyl-(4-methoxy-benzenesulfonyl)-amino]-methyl}-N-hydroxy-4-oxo-4-morpholine-1-yl-butyramide 3R-Cyclopentylmethyl-2S-{[ethyl-(4-methoxy-benzenesulfonyl)-amino]-methyl}-N-hydroxy-4-morpholine-4-yl-4-oxo-butyramide 3R-Cyclopentylmethyl-2S-{[(5-dimethyamino-naphthalene-1-sulfonyl)-methyl-amino]-methyl}-N-hydroxy-4-oxo-4-piperidine-1-yl-butyramide 3R-Cyclopentylmethyl-2S-{[(5-dimethyamino-naphthalene-1-sulfonyl)-methyl-amino]-methyl}-N-hydroxy-4-morpholine-4-yl-4-oxo-butyramide 2S-{[(5-Dimethylaminonaphthalene-1-sulfonyl)-ethyl-amino]-methyl}-5-methyl-3R-(morpholine-4-carbonyl)-hexanoic acid hydroxyamide 2S-{[(5-Dimethylaminonaphthalene-1-sulfonyl)-methyl-amino]-methyl}-5-methyl-3R-(piperidine-1-carbonyl)-hexanoic acid hydroxyamide 3R-Cyclopentylmethyl-2S-[(ethanesulfonyl-methyl-amino)-methyl]-N-hydroxy-4-oxo-4-piperidin-1-yl-butyramide 3R-Cyclopentylmethyl-N-hydroxy-2S-{[methyl-(propane-2-sulfonyl]-amino]-methyl}-4-oxo-4-piperidin-1-yl-butyramide 3R-Cyclopentylmethyl-N-hydroxy-2S-{[methyl-(octane-1-sulfonyl)-amino]-methyl}-4-oxo-4-piperidin-1-yl-butyramide 3R-Cyclopentylmethyl-N-hydroxy-2S-[(methyl-trifluoromethanesulfonyl-amino)-methyl]-4-oxo-4-piperidin-1-yl-butyramide 2S-{[(4-Chloro-benzenesulfonyl)-methyl-amino] methyl}-3R-cyclopentylmethyl-N-hydroxy-4-oxo-4-piperidin-1-yl-butyramide 3R-Cyclopentylmethyl-N-hydroxy-2S-{[methyl-(quinoline-8-sulfonyl)-amino]-methyl}-4-oxo-4-piperidin-1-yl-butyramide 3R-Cyclopentylmethyl-N-hydroxy-2S-{[methyl-(naphthalene-1-sulfonyl)-amino]-methyl}-4-oxo-4-piperidin-1-yl-butyramide 3R-Cyclopentylmethyl-N-hydroxy-2S-{[(isoquinoline-5-sulfonyl)-methyl-amino]-methyl}-4-oxo-4-piperidin-1-yl-butyramide 3R-Cyclopentylmethyl-2S-{[(6-dimethylamino-naphthalene-1-sulfonyl)-methyl-amino]-methyl}-N-hydroxy-4-oxo-4-piperidin-1-yl-butyramide 3R-Cyclopentylmethyl-2S-{[dimethylsulfamoyl-methyl-amino]-methyl}-N-hydroxy-4-oxo-4-piperidin-1-yl-butyramide 2S-[(Butyl-methanesulfonyl-amino)-methyl]-3R-cyclopentylmethyl-N-hydroxy-4-oxo-4-piperidin-1-yl-butyramide 3R-Cyclopentylmethyl-N-hydroxy-2S-[(isopropyl-methanesulfonyl)-amino)-methyl]-4-oxo-4-piperidin-1-yl-butyramide 2S-[(tert-Butyl-methanesulfonyl)-amino)-methyl]-3R-cyclopentylmethyl-N-hydroxy-4-oxo-4-piperidin-1-yl-butyramide 3R-Cyclopentylmethyl-N-hydroxy-2S-[(cyclopropyl-methanesulfonyl)-amino)-methyl]-4-oxo-4-piperidin-1-yl-butyramide 2S-[(Cyclopentyl-methanesulfonyl)-amino)-methyl]-3R-cyclopentylmethyl-N-hydroxy-4-oxo-4-piperidin-1-yl-butyramide and pharmaceutically acceptable salts hydrates and solvates thereof.

Compounds of the invention wherein V is HONH— may be prepared by a process which comprises causing an acid of the invention of general formula (IV)

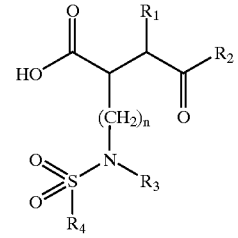

(IV)

or an activated derivative thereof to react with hydroxylamine, O-protected hydroxylamine, N,O-diprotected hydroxylamine, or a salt thereof, n, $R_1$, $R_2$, $R_3$, and $R_4$, being as defined in general formula (I) except that any substituents in $R_1$, $R_2$, $R_3$, and $R_4$ which are potentially reactive with hydroxylamine, the O-protected hydroxylamine, the N,O-diprotected hydroxylamine or their salts may themselves be protected from such reaction, then removing any protecting groups from the resultant hydroxamic acid moiety and from any protected substituents in $R_1$, $R_2$, $R_3$, and $R_4$.

Conversion of (IV) to an activated derivative such as the pentafluorophenyl, hydroxysuccinyl, or hydroxybenzotriazolyl ester may be effected by reaction with the appropriate alcohol in the presence of a dehydrating agent such as dicyclohexyl dicarbodiimide (DCC), N,N-dimethylaminopropyl-N'-ethyl carbodiimide (EDC), or 2-ethoxy-1-ethoxycarbonyl-1,2-dihydroquinoline (EEDQ).

Protecting groups as referred to above are well known per se, for example from the techniques of peptide chemistry. Amino groups are often protectable by benzyloxycarbonyl, t-butoxycarbonyl or acetyl groups, or in the form of a phthalimido group. Hydroxy groups are often protectable as readily cleavable ethers such as the t-butyl or benzyl ether, or as readily cleavable esters such as the acetate. Carboxy groups are often protectable as readily cleavable esters, such as the t-butyl or benzyl ester.

Examples of O-protected hydroxylamines for use in the process of the invention above include O-benzylhydroxylamine, O-4-methoxybenzylhydroxylamine, O-trimethylsilylhydroxylamine, and O-tert-butoxycarbonylhydroxylamine.

Examples of O,N-diprotected hydroxylamines for use in the process of the invention include N, O-bis(benzyl)hydroxylamine, N, O-bis(4-methoxybenzyl)hydroxylamine, N-tert-butoxycarbonyl-O-tert-butyldimethylsilylhydroxylamine, N-tert-butoxycarbonyl-O-tetrahydropyranylhydroxylamine, and N, O-bis(tert-butoxycarbonyl)hydroxylamine.

Acids of the invention (IV) differ in structure from the analogous compounds of EP-A-0684240 principally in that they have the above defined $R_4$—$(SO_2)$—$N(R_3)$—$(CH_2)_n$— group on the carbon atom carrying the carboxylic acid group. The synthetic route disclosed in that publication, which involves an alkylation step to introduce the desired group onto the carbon atom carrying the carboxyl group, may be used to prepare acids (IV) by substituting the alkylating agent required to introduce the $R_4$—$(SO_2)$—$N(R_3)$—$(CH_2)n$— group of this invention, for example $R_4$—$(SO_2)$—$N(R_3)$—$(CH_2)n$—Br.

Acids of the invention (IV) may also be prepared by forming the appropriate $R_4$-sulfonamide of an amine of formula (V), for example by reaction with an activated derivative of a sulphonic acid (VI),

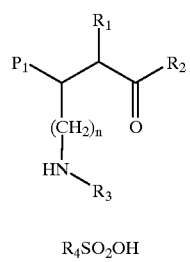

(V)

$R_4SO_2OH$ (VI)

wherein $P_1$ is a protected carboxyl group and n, $R_1$, $R_2$, $R_3$ and $R_4$ are as defined in relation to formula (I) except that any substituents in $R_1$, $R_2$, $R_3$ and $R_4$ which are potentially reactive with (VI) may be protected, and thereafter deprotecting the protected carboxyl group $P_1$ and any protected substituents in $R_1$, $R_2$, $R_3$ and $R_4$. Activated sulphonic acids and conditions for forming sulfonamides are well known in organic synthesis, e.g. reaction with the sulfonyl chloride in the presence of an organic base.

Amines of formula (V) in which $R_3$ is hydrogen may be prepared from the corresponding hydroxyl compound of formula (VA)

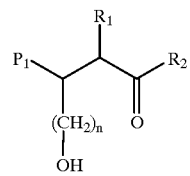

(VA)

by methods known in organic synthesis for conversion of hydroxyl groups to amine groups, e.g. by conversion the hydroxyl group of (VIA) to a leaving group, displacement with azide, followed by catalytic hydrogenation of the azide group.

Amines of formula (V) in which $R_3$ is other than hydrogen may be accessible by direct introduction of $R_3$ onto the amine group of the compound (V) wherein $R_3$ is hydrogen. In the special case of compounds (V) wherein n is 1, ammination of the double bond of compounds (VIA)

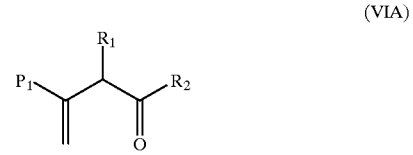

(VIA)

with the amine $R_3NH_2$ can provide a convenient route.

Compounds (VIA) and (VIA) may be prepared by reaction of a cyclic amine $R_2H$ with the corresponding carboxylic acids (VAB) and (VIIB)

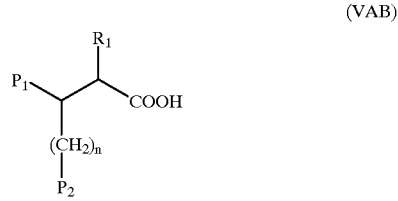

(VAB)

(VIB)

wherein n, $P_1$, $R_1$, and $R_2$ are as defined in relation to formula (V) and $P_2$ is a protected hydroxyl group, which is converted to the required hydroxyl group after the reaction with amine $R_2H$.

Compounds (VAB) and (VIIB) are either known, are analogues of known compounds, or are accessible by known literature methods.

As mentioned above, compounds of formula (I) are useful in human or veterinary medicine since they are active as inhibitors of MMPs. Enzyme inhibition assays useful for determining the activity of a particular compound of the invention against MMPs are known, see for example the assays described in Biological Example A below, and the MMP inhibition assays described in patent publications listed above in the section "Background to the Invention".

Accordingly in another aspect, this invention concerns:

(i) a method of management (by which is meant treatment or prophylaxis) of diseases or conditions mediated by MMPs in mammals, in particular in humans, which method comprises administering to the mammal an effective amount of a compound as defined with respect to formula (I) above, or a pharmaceutically acceptable salt thereof; and (ii) a compound as defined with respect to formula (I) for use in human or veterinary medicine, particularly in the management (by which is meant treatment or prophylaxis) of diseases or conditions mediated by MMP; and (iii) the use of a compound as defined with respect to formula (I) in the preparation of an agent for the management (by which is meant treatment or prophylaxis) of diseases or conditions mediated by MMPs.

Diseases or conditions mediated by MMPs include those involving tissue breakdown such as bone resorption, inflammatory diseases, dermatological conditions and tumour invasion by secondary metastases, in particular rheumatoid arthritis, osteoarthritis, periodontitis, gingivitis, corneal ulceration and tumour invasion by secondary metastases as well as neuroinflammatory disorders, including those involving myelin degradation, for example multiple sclerosis.

In a further aspect of the invention there is provided a pharmaceutical or veterinary composition comprising a compound of formula (I) together with a pharmaceutically or veterinarily acceptable excipient or carrier.

One or more compounds of general formula (I) may be present in the composition together with one or more excipient or carrier.

It will be understood that the specific dose level for any particular patient will depend upon a variety of factors including the activity of the specific compound employed, the age, body weight, general health, sex, diet, time of administration, route of administration, rate of excretion, drug combination and the severity of the particular disease undergoing therapy. Optimum dose levels and frequency of dosing will be determined by clinical trial.

The compounds with which the invention is concerned may be prepared for administration by any route consistent with their pharmacokinetic properties. The orally administrable compositions may be in the form of tablets, capsules, powders, granules, lozenges, liquid or gel preparations, such as oral, topical, or sterile parenteral solutions or suspensions. Tablets and capsules for oral administration may be in unit dose presentation form, and may contain conventional excipients such as binding agents, for example syrup, acacia, gelatin, sorbitol, tragacanth, or polyvinyl-pyrrolidone; fillers for example lactose, sugar, maize-starch, calcium phosphate, sorbitol or glycine; tabletting lubricant, for example magnesium stearate, talc, polyethylene glycol or silica; disintegrants for example potato starch, or acceptable wetting agents such as sodium lauryl sulphate. The tablets may be coated according to methods well known in normal pharmaceutical practice. Oral liquid preparations may be in the form of, for example, aqueous or oily suspensions, solutions, emulsions, syrups or elixirs, or may be presented as a dry product for reconstitution with water or other suitable vehicle before use. Such liquid preparations may contain conventional additives such as suspending agents, for example sorbitol, syrup, methyl cellulose, glucose syrup, gelatin hydrogenated edible fats; emulsifying agents, for example lecithin, sorbitan monooleate, or acacia; non-aqueous vehicles (which may include edible oils), for example almond oil, fractionated coconut oil, oily esters such as glycerine, propylene glycol, or ethyl alcohol; preservatives, for example methyl or propyl p-hydroxybenzoate or sorbic acid, and if desired conventional flavouring or colouring agents.

For topical application to the skin, the drug may be made up into a cream, lotion or ointment. Cream or ointment formulations which may be used for the drug are conventional formulations well known in the art, for example as described in standard textbooks of pharmaceutics such as the British Pharmacopoeia.

For topical application to the eye, the drug may be made up into a solution or suspension in a suitable sterile aqueous or non aqueous vehicle. Additives, for instance buffers such as sodium metabisulphite or disodium edeate; preservatives including bactericidal and fungicidal agents such as phenyl mercuric acetate or nitrate, benzalkonium chloride or chlorhexidine, and thickening agents such as hypromellose may also be included.

The active ingredient may also be administered parenterally in a sterile medium. Depending on the vehicle and concentration used, the drug can either be suspended or dissolved in the vehicle. Advantageously, adjuvants such as a local anaesthetic, preservative and buffering agents can be dissolved in the vehicle.

The following Examples illustrate embodiments of the invention.

2-Benzyloxycarbonyl-3R-carboxy-5-methyl-hexanoic acid 1-benzyl ester 4-tert-butyl ester was prepared as described in EP 0 446 267. 2S-Allyl-3R-isobutyl-succinic acid 1-tert-butyl ester dicyclohexylamine salt was prepared as described in WO 96/06074.

The following abbreviations have been used throughout:
9-BBN 9-Borabicyclo[3.3.1]nonane
DMF N,N-Dimethylformamide
EDC N-Ethyl-N'-(3-dimethylaminopropyl)-carbodiimide
HOBt 1-Hydroxybenzotriazole
NMM N-Methylmorpholine
TFA Trifluoroacetic acid
THF Tetrahydrofuran
TLC Thin Layer Chromatography
Z-ONSu N-(Benzyloxycarbonyloxy)-succinimide $^1$H and $^{13}$C NMR spectra were recorded using a Bruker AC 250E spectrometer at 250.1 and 62.9 MHz, respectively. Elemental microanalyses were performed by Medac Ltd. (Department of Chemistry, Brunel University, Uxbridge, Middlesex UB8 3PH). Preparative HPLC was performed using a Gilson system.

EXAMPLE 1
2S-[3-(4-Methoxybenzenesulfonyl-amino)-propyl]-5-methyl-3R-(piperidine-1-carbonyl)-hexanoic acid hydroxyamide
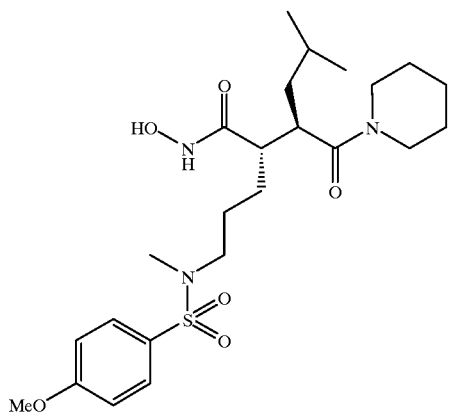
The title compound was prepared according to the route outlined in Scheme 1 and is described in detail below.
Scheme 1
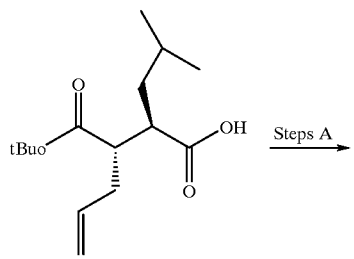
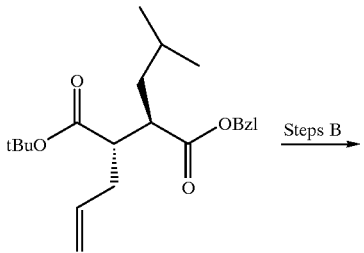
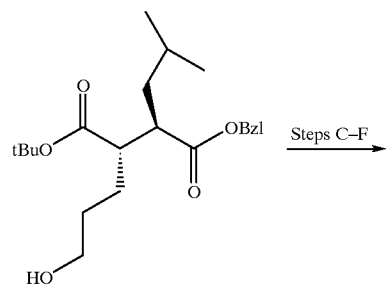
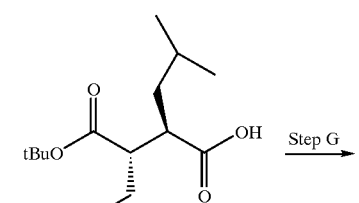
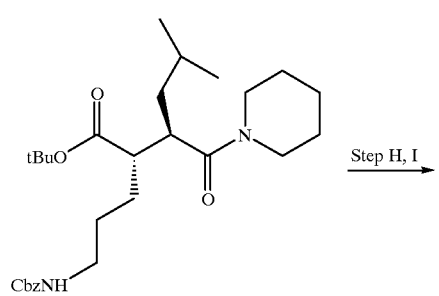

-continued

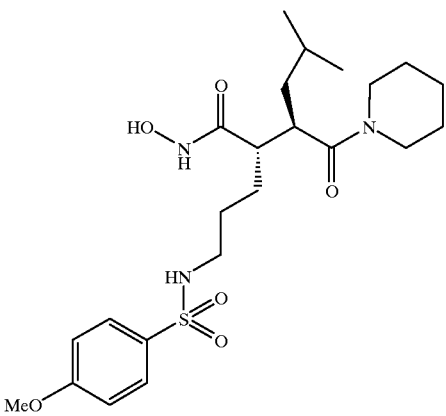

Reagents and conditions:
(A) BzI—Br, K$_2$CO$_3$ in acetone;
(B) 9-BBN, H$_2$O$_2$ in THF;
(C) MsCl, Et$_3$N in THF, 0° C.;
(D) NaN$_3$, $^n$Bu$_4$I, in toluene/water, reflux;
(E) H$_2$, 10% Pd/C in ethanol;
(F) Z—ONSu, Et$_3$N, THF;
(G) piperidine EDC, HOBt, THF;
(H) H$_2$, 10% Pd/C in ethanol;
(I) 4-MeO(C$_6$H$_4$)SO$_2$Cl, Et$_3$N in THF;
(J) TFA in CH$_2$Cl$_2$, 4° C.;
(K) HOBt, EDC in DMF, then H$_2$NOH·HCl, NMM.

Step A: 2S-Allyl-3R-isobutyl-succinic acid 4-benzyl ester 1-tert-butyl ester

2S-Allyl-3R-isobutyl-succinic acid 1-tert-butyl ester dicyclohexylamine salt (31.6 g, 70 mmol) was partitioned between dichloromethane and 1M hydrochloric acid. The organic phase was washed with water, dried, filtered and concentrated to dryness. The resulting free acid (18.6 g) was dissolved in acetone (250 ml) and the solution was placed under an argon atmosphere. Potassium carbonate (19 g, 138 mmol) and benzyl bromide (7.4 ml, 62.2 mmol) were added and the reaction mixture was stirred overnight. The solvent was removed under reduced pressure and the residual oil was dissolved in ethyl acetate. The solution was washed with water (3×50 ml), dried over anhydrous sodium sulphate and filtered. The filtrate was concentrated to dryness and the residue was purified by flash chromatography (silica gel, ethyl acetate hexane, 1:9) to provide the title compound as a colourless oil (21.7 g, 88%). $^1$H-NMR: δ (CDCl$_3$), 7.41–7.30 (5H, m), 5.70 (1H, m), 5.14 (2H, d, J=1.3 Hz), 5.06–4.94 (2H, m), 2.75 (1H, m), 2.60 (1H, m), 2.45 (1H, m), 2.12 (1H, m), 1.71 (1H, m), 1.43 (9H, s), 1.32–1.11 (2H, m), 0.88 (3H, d, J=6.5 Hz) and 0.86 (3H, d, J=6.6 Hz).

Step B: 2S-(3-Hydroxypropyl)-3R-isobutyl-succinic acid 4-benzyl ester 1-tert-butyl ester 2S-Allyl-3R-isobutyl-succinic acid 4-benzyl ester 1-tert-butyl ester (7.42 g, 20.6 mmol) was dissolved in a 0.5M solution of 9-BBN in THF (100 ml, 50 mmol) at room temperature and allowed to stir for 3 days. The solution was treated with 3M sodium hydroxide solution (10 ml, 30 mmol) followed by 30% w/v hydrogen peroxide (slowly) and the reaction mixture was allowed to stir for a further 2 hours. THF was evaporated under reduced pressure and the residue was diluted with ethyl acetate (100 ml) and water (50 ml). The organic layer was separated, washed with water (3×50 ml), dried over anhydrous sodium sulfate and filtered. Concentration under reduced pressure gave an oil which was purified by flash chromatography (silica gel, ethyl acetate-hexane, 3:7). Colourless oil (5.3 g, 68%). $^1$H-NMR: δ (CDCl$_3$), 7.38–7.41 (5H, m), 5.13 (2H, s), 3.63–3.53 (1H, m), 3.53 (2H, t, J=6.1 Hz), 2.68–2.80 (1H, m), 2.57–2.44 (1H, m), 1.77–1.31 (6H, m), 1.44 (9H, s), 1.22–1.10 (1H, m), 0.88 (3H, d, J=5.9 Hz) and 0.85 (3H, d, J=6.2 Hz).

Step C: 3R-Isobutyl-2S-(3-methanesulfonyloxy-propyl)-succinic acid 4-benzyl ester 1-tert-butyl ester 2S-(3-Hydroxypropyl)-3R-isobutyl-succinic acid 4-benzyl ester 1-tert-butyl ester (5.3 g, 14 mmol) was dissolved in dry THF (150 ml) and the solution was cooled to 0° C. Triethylamine (2.1 ml, 15.1 mmol) was added followed by methanesulfonyl chloride (1.2 ml, 15.5 mmol) and the reaction mixture was allowed to warm slowly to room temperature before stirring overnight. The solvents was removed under reduced pressure and the residue was dissolved in ethyl acetate (150 ml). The organic solution was washed with water (3×50 ml), dried over anhydrous sodium sulfate and filtered and concentrated in vacuo to leave the title compound (6.1 g, 95%) which was used without further purification. $^1$H-NMR: δ (CDCl$_3$), 7.40–7.30 (5H, m), 5.13 (2H, s), 4.15–4.06 (2H, m), 2.95 (3H, s), 2.76 (1H, m), 2.49 (1H, m), 1.83–1.33 (6H, m), 1.44 (9H, s), 1.16 (1H, m), 0.87 (3H, d, J=6.4 Hz) and 0.85 (3H, d, J=5.3 Hz).

Step D: 2S-(3-Azido-propyl)-3R-isobutyl-succinic acid 4-benzyl ester 1-tert-butyl ester 3S-Isobutyl-2R-(3-methanesulfonyloxy-propyl)-succinic acid 4-benzyl ester 1-tert-butyl ester (6.1 g, 14 mmol) was dissolved in toluene (100 ml) and tetrabutylammonium iodide (4.9 g, 14 mmol) was added followed by a solution of sodium azide (8.7 g, 140 mmol) in water (100 ml). The reaction mixture was heated at reflux for 8 hours, stirred at room temperature for 3 days then heated at reflux for a further 6 hours. The reaction mixture was diluted with ethyl acetate (100 ml) and the organic layer was separated, washed with water (3×80 ml), dried over anhydrous sodium sulfate, filtered and evaporated under reduced pressure. The product thus obtained (5.5 g, 95%) was used without further purification. $^1$H-NMR: δ (CDCl$_3$), 7.42–7.30 (5H, m), 5.15 (2H, s), 3.28–3.10 (2H, m), 2.76 (1H, m), 2.48 (1H, m), 1.79–1.28 (6H, m), 1.45 (9H, s), 1.16 (1H, m), 0.89 (3H, d, J=6.1 Hz), and 0.86 (3H, d, J=5.9 Hz).

Step E: 2S-(3-Amino-propyl)-3R-isobutyl-succinic acid 1-tert-butyl ester 2S-(3-Azido-propyl)-3R-isobutyl-succinic acid 4-benzyl ester 1-tert-butyl ester (5.5 g, 12.7 mmol) was dissolved in ethanol (100 ml) and the solution was placed under an argon atmosphere. 10% Palladium on charcoal (800 mg) was added and hydrogen was introduced by bubbling into the suspension. The reaction mixture was stirred overnight under an atmosphere of hydrogen. The system was purged with argon and the catalyst was removed by filtration. The solution was concentrated in vacuo, whereupon $^1$H-NMR analysis revealed that the reaction was incomplete. Hydrogenolysis was repeated exactly as described above to provide the title compound as an amorphous solid (3.7 g, ca. quant.). $^1$H-NMR: δ (CDCl$_3$), 5.19–4.85 (2H, br s), 3.17–2.93 (2H, m), 2.69 (1H, m), 2.44 (1H, m), 1.89–1.40 (6H, m), 1.46 (9H, s), 1.12 (1H, m), 0.89 (3H, d, J=6.2 Hz) and 0.88 (3H, d, J=6.2 Hz).

Step F: 2S-(3-Benzyloxycarbonylamino-propyl)-3R-isobutyl-succinic acid 1-tert-butyl ester 2S-(3-Amino-propyl)-3R-isobutyl-succinic acid 1-tert-butyl ester (3.7 g, 12.9 mmol) was dissolved in THF (150 ml) and the solution was cooled to 0° C. Triethylamine (3.8 ml, 27.3 mmol) and Z-ONSu (3.5 g, 14 mmol) were added and the mixture was stirred overnight at room temperature. The solvent was removed under reduced pressure and the residue was dissolved in ethyl acetate (150 ml), washed successively with 1M hydrochloric acid (50 ml) and water (2×30 ml) dried over anhydrous sodium sulfate and filtered. Concentration under reduced pressure afforded the title compound contaminated with excess Z-ONSu, which could not be separated by column chromatography or acid-base extraction. The crude mixture was therefore dissolved in THF (100 ml) and treated with N,N-dimethylethylenediamine (0.18 ml, 1.6 mmol) with stirring overnight at room temperature. The by-products were then conveniently removed by acid extraction from ethyl acetate, to leave the pure title compound (2.43 g, 66%) after removal of solvent. $^1$H-NMR: δ (CDCl$_3$), 7.41–7.27 (5H, m), 5.09 (2H, s), 4.93 (1H, m), 3.28–3.13 (2H, m), 2.70 (1H, m), 2.50 (1H, m), 1.78–1.40 (6H, m), 1.45 (9H, s), 1.12 (1H, m), 0.90 (3H, d, J=6.3 Hz) and 0.90 (3H, d, J=6.3 Hz).

Step G: 2S-(3-Benzyloxycarbonylamino-propyl)-5-methyl-3R-(piperidine-1-carbonyl)-hexanoic acid tert-butyl ester 2S-(3-Benzyloxycarbonylamino-propyl)-3R-isobutyl-succinic acid 1-tert-butyl ester (2.43 g, 5.8 mmol) was dissolved in DMF (150 ml) and the solution was cooled to 0° C. before the addition of HOBt (0.9 g, 6.6 mmol) and EDC (1.3 g, 6.8 mmol). The reaction was stirred for 1 hour, after which piperidine (1.1 ml, 11.1 mmol) was added and stirring continued overnight. The solvent was removed in vacuo and the title compound was isolated by extraction followed by flash chromatography (silica gel, ethyl acetate-hexane, 4:6). Colourless oil (2.34 g, 83%). $^1$H-NMR: δ (CDCl$_3$), 7.40–7.29 (5H, m), 5.08 (2H, s), 4.92 (1H, m), 3.62–3.49 (4H, m), 3.28–3.10 (2H, m), 3.05 (1H, m), 2.51 (1H, m), 1.87–1.30 (12H, m), 1.47 (9H, s), 1.08 (1H, m), 0.86 (3H, d, J=6.5 Hz) and 0.86 (3H, d, J=6.5 Hz).

Step H: 2S-(3-Amino-propyl)-5-methyl-3R-(piperidine-1-carbonyl)-hexanoic acid tert-butyl ester 2S-(3-Benzyloxycarbonylamino-propyl)-5-methyl-3R-(piperidine-1-carbonyl)-hexanoic acid tert-butyl ester (2.34 g, 4.8 mmol) was Z-deprotected by hydrogenolysis as described in Step E to provide the title compound as a colourless oil (1.70 g, quant.). $^1$H-NMR: δ (CDCl$_3$), 3.73–3.50 (4H, m), 3.04 (1H, m), 2.73– 2.60 (2H, m), 2.51 (1H, m), 1.88–1.31 (12H, m), 1.46 (9H, s), 1.08 (1H, m), 0.85 (3H, d, J=6.5 Hz) and 0.85 (3H, d, J=6.5 Hz).

Step I: 2S-[3-(4-Methoxybenzenesulfonyl-amino)-propyl]-5-methyl-3R-(piperidine-1-carbonyl)-hexanoic acid tert-butyl ester 2S-(3-Amino-propyl)-5-methyl-3R-(piperidine-1-carbonyl)-hexanoic acid tert-butyl ester (1.70 g, 4.8 mmol) was converted to the title sulfonamide by a similar method to that described in Step C, substituting 4-methoxybenzenesulfonyl chloride for methanesulfonyl chloride. The desired product was isolated as a colourless gum (1.53 g, 61%) by extraction followed by flash chromatography (silica gel, ethyl acetate-hexane, 6:4). $^1$H-NMR: δ (CDCl$_3$), 7.73 (2H, d, J=9.0 Hz), 6.90 (2H, d, J=8.8 Hz), 5.33 (1H, t, J=6.2 Hz), 3.80 (3H, s), 3.62–3.44 (4H, m), 2.97 (1H, m), 2.90–2.72 (2H, m), 2.39 (1H, m), 1.76–1.21 (12H, m), 1.37 (9H, s), 0.99 (1H, m), 0.79 (3H, d, J=6.4 Hz) and 0.79 (3H, d, J=6.4 Hz).

Step J: 2S-[3-(4-Methoxybenzenesulfonyl-amino)-propyl]-5-methyl-3R-(piperidine-1-carbonyl)-hexanoic acid 2S-[3-(4-Methoxybenzenesulfonyl-amino)-propyl]-5-methyl-3R-(piperidine-1-carbonyl)-hexanoic acid tert-butyl ester (1.53 g, 2.9 mmol) was dissolved in dichloromethane (15 ml) and TFA (15 ml) was added. The reaction mixture was stored at 4° C. overnight. The solvent was removed under reduced pressure and residual TFA was removed by azeotroping with toluene followed by diisopropyl ether. The resulting white waxy solid was used in Step K without further purification (1.37 g, contains residual solvent). $^1$H-NMR: δ (CDCl$_3$), 7.78 (2H, d, J=9.0 Hz), 6.97 (2H, d, J=8.9 Hz), 3.87 (3H, s), 3.70–3.50 (5H, m), 3.08 (1H, m), 2.90 (2H,t, J=6.3 Hz), 2.62 (1H, m), 1.85–1.37 (12H, m), 1.26 (1H, m), 0.88 (3H, d, J=6.4 Hz) and 0.88 (3H, d, J=6.4 Hz).

Step K: 2S-[3-(4-Methoxybenzenesulfonyl-amino)-propyl]-5-methyl-3R-(piperidine-1-carbonyl)-hexanoic acid hydroxyamide 2S-[3-(4-Methoxybenzenesulfonyl-amino)-propyl]-5-methyl-3R-(piperidine-1-carbonyl)-hexanoic acid (2.9 mmol) was dissolved in DMF (25 ml) and the solution was cooled to 0° C. before addition of HOBt (0.6 g, 4.4 mmol) and EDC (0.85 g, 4.4 mmol). The reaction mixture was stirred for 30 minutes after which hydroxylamine hydrochloride (0.4 g, 5.7 mmol) and NMM (0.64 ml, 5.9 mmol) were added. The reaction mixture was allowed to warm to room temperature and then stirred for 3 days. The solvent was removed in vacuo and the residue was partitioned between dissolved in ethyl acetate and water. The organic layer was washed successively with sat. aq. sodium hydrogen carbonate and water, dried over anhydrous sodium sulfate and filtered and concentrated under reduced pressure. The desired product was isolated by flash chromatography (acid-washed silica gel, 5% methanol in dichloromethane) followed by extraction to remove remaining traces of HOBt. Colourless gum (300 mg, 21%). $^1$H-NMR: δ ((CD$_3$)$_2$SO), 10.53 (1H, d, J=1.4 Hz), 8.83 (1H, d, J=1.6 Hz), 7.69 (2H, d, J=8.8 Hz), 7.40 (1H, t, J=5.9 Hz), 7.09 (2H, d, J=8.9 Hz), 3.83 (3H, s), 3.57–3.40 (4H, m), 2.97 (1H, m), 2.68–2.48 (2H, m), 2.04 (1H, m), 1.63–1.06 (12H, m), 0.96 (1H, m), 0.77 (3H, d, J=6.4 Hz) and 0.77 (3H, d, J=6.4 Hz). $^{13}$C-NMR: δ ((CD$_3$)$_2$SO), 176.9, 174.8, 167.0, 137.4, 133.6, 119.3, 64.8, 60.6, 51.9, 51.4, 47.6, 47.2, 35.5, 32.9, 31.4, 30.6, 29.2, 29.0, 26.7 and 19.1. IR: ν$_{max}$(KBr) 3206, 2940, 1659, 1599 and 1464 cm$^{-1}$. Found: C 55.23%, H 7.51%, N 8.14%; C$_{23}$H$_{37}$N$_3$O$_6$S.0.9H$_2$O requires C 55.27%, H 7.82%, N 8.41%.

EXAMPLE 2

2S-[(4-Methoxybenzenesulfonyl-amino)-ethyl]-5-methyl-3R-(piperidine-1-carbonyl)-hexanoic acid hydroxyamide

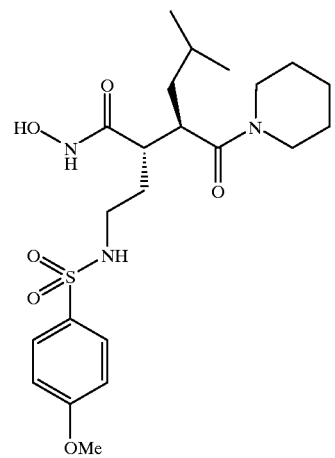

The title compound was prepared from 2S-(2-hydroxyethyl)-3R-isobutyl-succinic acid 4-benzyl ester 1-tert-butyl ester by analogy with Example 1 (Steps C–K). White solid. m.p. 134–136° C. $^1$H-NMR: δ ((CD$_3$)$_2$SO), 10.46 (1H, s), 8.89 (1H, d, J=1.3 Hz), 7.67 (2H, d, J=8.9 Hz), 7.43 (1H, t, J=5.7 Hz), 7.11 (2H, d, J=8.8 Hz), 3.84 (3H, s), 3.57–3.30 (4H, m), 2.93 (1H. m), 2.68–2.38 (2H, m), 2.04 (1H, m), 1.67–1.13 (10H, m), 0.96 (1H. m), 0.76 (3H, d, J=6.5 Hz) and 0.76 (3H, d, J=6.5 Hz). $^{13}$C-NMR: δ ((CD$_3$)$_2$SO), 176.6, 174.3, 167.1, 137.3, 133.6, 119.4, 60.7, 51.4, 49.9, 47.2, 45.8, 35.4, 31.4, 30.6, 30.5, 29.2, 28.9 and 26.7. IR: $v_{max}$(KBr) 3219, 2942, 1669, 1598, 1446 and 1259 cm$^{-1}$. Found: C 55.69%, H 7.59%, N 8.86%; C$_{22}$H$_{35}$N$_3$O$_6$S.0.3H$_2$O requires C 55.63%, H 7.55%, N 8.85%.

The starting material was prepared as follows:

2S-Allyl-3R-isobutyl-succinic acid 4-benzyl ester 1-tert-butyl ester (Example 1, Step A) (5.0 g, 13.9 mmol) was dissolved in dichloromethane (75 ml) and cooled in an dry ice/acetone bath. Ozone was bubbled through the solution for 25 minutes, at which time the solution turned blue and TLC analysis revealed that all of the starting material had been consumed. The solution was purged with argon and warmed slowly to room temperature. The solution was diluted with methanol (50 ml) and cooled to 0° C. Sodium borohydride (2.6 g, 69.3 mmol) was added portionwise with stirring. Vigorous effervescence occurred and the reaction mixture was allowed to warm to room temperature and stirred for 2 hours to ensure complete reaction. The reaction was quenched by addition of saturated aq. ammonium chloride and the organic solvents were removed by evaporation under reduced pressure. The aqueous phase was extracted with three times with ethyl acetate. The combined organic extracts were washed with 1M hydrochloric acid and brine, dried over anhydrous magnesium sulfate, filtered and concentrated to provide 2S-(3-hydroxyethyl)-3R-isobutyl-succinic acid 4-benzyl ester 1-tert-butyl ester as a colourless oil (5.8 g, 72%). $^1$H-NMR: δ (CDCl$_3$), 7.40–7.31 (5H, s), 5.14 (2H, s), 3.60 (2H, t, J=6.3 Hz), 2.79 (1H, dt, J=3.6, 9.9 Hz), 2.64 (1H, dt, J=3.5, 9.9 Hz), 1.91–1.52 (4H, m), 1.45 (9H, s), 1.17 (1H, m), 0.89 (3H, d, J=6.0 Hz) and 0.86 (3H, d, J=6.3 Hz).

EXAMPLE 3

2S-(2-Methanesulfonylamino-ethyl)-5-methyl-3R-(piperidine-1-carbonyl)-hexanoic acid hydroxyamide

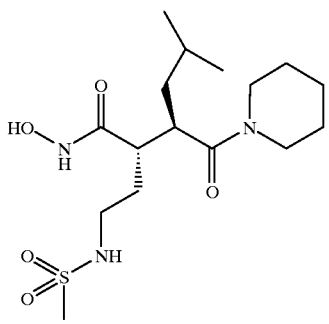

The title compound was prepared from 2S-(2-Hydroxyethyl)-3R-isobutyl-succinic acid 4-benzyl ester 1-tert-butyl ester by analogy with Example 2, using methanesulfonyl chloride in lieu of 4-methoxybenzenesulfonyl chloride. Off-white solid. m.p. 75–80° C. $^1$H-NMR: δ (CD$_3$OD), 3.71–3.44 (4H, m), 3.18 (1H, dt, J=3.2, 7.4 Hz), 2.84 (3H, s), 2.96–2.72 (2H, m), 2.24 (1H, dt, J=3.3, 7.5 Hz), 1.88–1.21 (10H, m), 1.02 (1H, dt, J=3.2, 6.7 Hz), 0.77 (3H, d, J=6.4 Hz) and 0.77 d, J=6.5 Hz). $^{13}$C-NMR: δ ( CD$_3$OD), 176.9, 174.8, 70.5, 54.1, 50.9, 48.8, 46.7, 44.7, 44.4, 44.1, 42.1, 34.5, 30.4, 29.5, 29.4, 27.9, 26.7 and 24.6. IR: $v_{max}$ (KBr) 3224, 2936, 1605, 1450, 1318 and 1150 cm$^{-1}$.

EXAMPLE 4

2S-{3-[(4-Methoxybenzenesulfonyl)-methyl-amino]-propyl}-5-methyl-3R-(piperidine-1-carbonyl)-hexanoic acid hydroxyamide

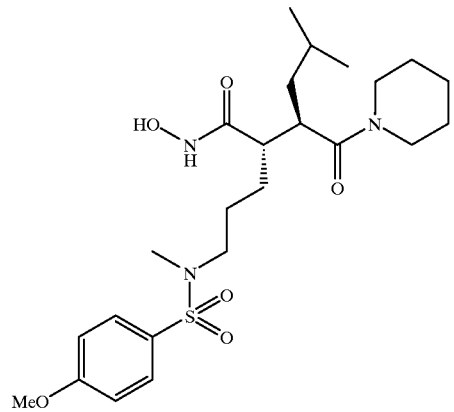

The title compound was prepared from 2S-{3-[(4-Methoxybenzenesulfonyl)-methyl-amino]-propyl}-5-methyl-3R-(piperidine-1-carbonyl)-hexanoic acid tert-butyl ester by analogy with Example 1 (Steps J and K). White crystalline solid. m.p. 159–161° C. $^1$H-NMR: δ ((CD$_3$)$_2$SO), 10.54 (1H, s), 8.85 (1H, d, J=1.2 Hz), 7.67 (2H, d, J=8.8 Hz), 7.12 (2H, d, J=8.9 Hz), 3.84 (3H, s), 3.68–3.31 (4H, m), 3.01 (1H, m), 2.74 (2H, m), 2.54 (3H, s), 2.10 (1H, m), 1.68–0.90 (12H, m), 0.78 (3H, d, J=6.4 Hz) and 0.78 (3H, d, J=6.4 Hz). $^{13}$C-NMR: δ ((CD$_3$)$_2$SO), 176.9, 174.8, 167.5, 134.3, 133.8, 119.6, 60.7, 54.6, 51.9, 51.5, 47.2, 39.6, 32.6, 31.3, 30.5, 30.4, 29.2, 29.0 and 26.7. IR: $v_{max}$(KBr) 3217, 2950, 1662, 1608, 1463, 1339 and 1256 cm$^{-1}$. Found: C 55.23%, H 7.51%, N 8.14%; C$_{24}$H$_{39}$N$_3$O$_6$S.0.9H$_2$O requires C 55.27%, H 7.82%, N 8.41%.

The starting material was prepared as follows:

To a solution of 2S-[3-(4-Methoxybenzenesulfonyl-amino)-propyl]-5-methyl-3R-(piperidine-1-carbonyl)-hexanoic acid tert-butyl ester (Example 1, STEP I) (4 g, 7.6 mmol) in THF (40 ml) and water (4 ml) was added potassium hydroxide (430 mg, 7.7 mmol) and dimethyl sulfate (0.72 ml, 7.6 mmol) and the reaction mixture was stirred overnight at room temperature. The solvents were removed under reduced pressure, the residue was dissolved in ethyl acetate (150 ml) and washed with water. (4×30 ml). The organic layer was dried over anhydrous sodium sulfate, filtered, evaporated to leave an oil. $^1$H NMR analysis revealed that the reaction was incomplete. The alkylation procedure was repeated to afford the desired product (4 g, 99%) as a colourless gum after column chromatography. $^1$H-NMR: δ (CDCl$_3$), 7.69 (2H, d, J=9.0 Hz), 6.97 (2H, d, J=8.8 Hz), 3.87 (3H, s), 3.66–3.54 (4H, m), 3.06 (1H, dt, J=2.9, 10.7 Hz), 2.99–2.88 (2H, m), 2.64 (3H, s), 2.48 (1H, m) (1H, m), 1.72–1.31 (11H, m), 1.46 (9H, s), 1.05 (1H, m), 0.86 (3H, d, J=6.6 Hz) and 0.86 (3H, d, J 6.6 Hz).

The following additional compounds were prepared by analogy with Example 4, starting from the appropriate intermediates:

EXAMPLE 5

2S-{2-[(4-Methoxy-benzenesulfonyl)-methyl-amino]-ethyl}-5-methyl-3R-(piperidine-1-carbonyl)-hexanoic acid hydroxyamide

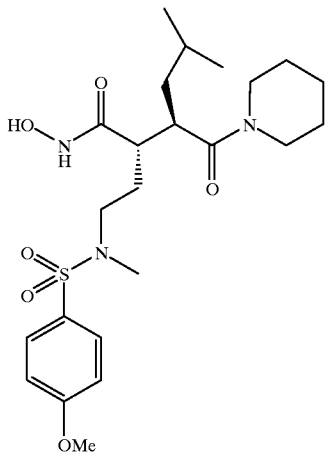

From 2S-[2-(4-methoxybenzenesulfonyl-amino)-ethyl]-5-methyl-3R-(piperidine-1-carbonyl)-hexanoic acid tert-butyl ester (Example 2). White amorphous solid. m.p. 87–89° C. $^{1}$H-NMR: δ ((CD$_3$)$_2$SO), 8.88 (1H, d, J=1.3 Hz), 7.64 (2H, d, 7.13 (2H, d, J=9.0 Hz), 3.84 (3H, s), 3.59–3.38 (4H, m), 3.03–2.78 (2H, m), 2.61 (1H, m), 2.56 (3H, s), 2.12 (1H, m), 1.70–1.17 (10H, m), 0.99 (1H, m), 0.77 (3H, d, J=6.5 Hz) and 0.77 (3H, d, J=6.5 Hz). $^{13}$C-NMR: δ ((CD$_3$)$_2$SO), 176.6, 174.2, 167.6, 134.3, 133.7, 119.6, 60.7, 53.0, 51.4, 49.7, 47.2, 39.6, 33.3, 31.5, 30.7, 30.5, 29.1, 28.9, 26.7, 25.8 and 19.1. IR: $v_{max}$(KBr) 3214, 2938, 2866, 1699, 1459 and 1158 cm$^{-1}$. Found: C 55.94%, H 7.62%, N 8.35%; C$_{23}$H$_{37}$N$_3$O$_6$S.0.6H$_2$O requires C 55.87%, H 7.79%, N 8.50%.

EXAMPLE 6

2S-[2-(Methanesulfonyl-methyl-amino)-ethyl]-5-methyl-3R-(piperidine-1-carbonyl)-hexanoic acid hydroxyamide

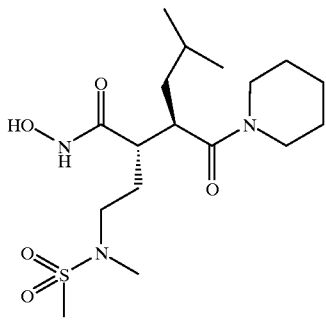

From 2S-(2-Methanesulfonylamino-ethyl)-5-methyl-3R-(piperidine-1-carbonyl)- hexanoic acid tert-butyl ester (Example 3). Off-white solid. m.p. 75–80° C. $^{1}$H-NMR: δ (CD$_3$OD), 3.62–3.50 (4H, m), 3.13 (1H, dt, J=3.4, 7.3 Hz), 3.05–2.82 (2H, m), 2.71 (3H, s), 2.66 (3H, s), 2.20 (1H, m), 1.69–1.38 (10H, m), 0.98 (1H, m), 0.78 (3H, d, J=6.4 Hz) and 0.77 (3H, d, J=6.4 Hz). $^{13}$C-NMR: δ (CD$_3$OD), 176.9, 174.8, 50.9, 48.6, 46.7, 44.6, 44.1, 37.5, 37.4, 32.4, 30.4, 29.5, 29.5, 27.9, 26.9 and 24.7. IR: $v_{max}$(KBr) 3213, 2943, 1716, 1605, 1470, 1330, 1152, 968, 779 and 514 cm$^{-1}$.

EXAMPLE 7

2S-{[(4-Methoxybenzenesulfonyl)-methyl-amino]-methyl}-5-methyl-3R-(piperidine-1-carbonyl)-hexanoic acid hydroxyamide

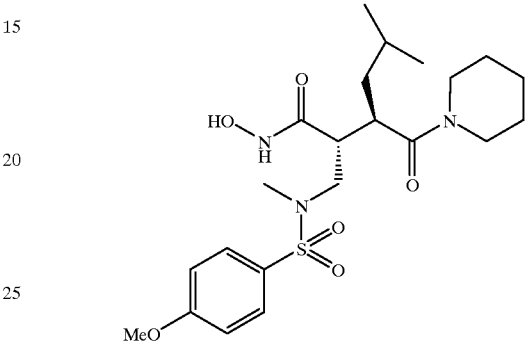

The title compound was prepared according to the route outlined in Scheme 2 and is described in detail below.

Scheme 2

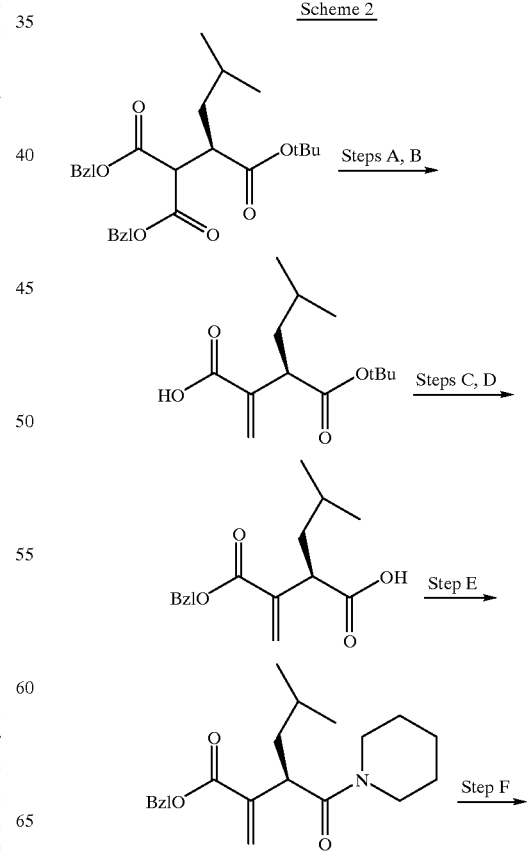

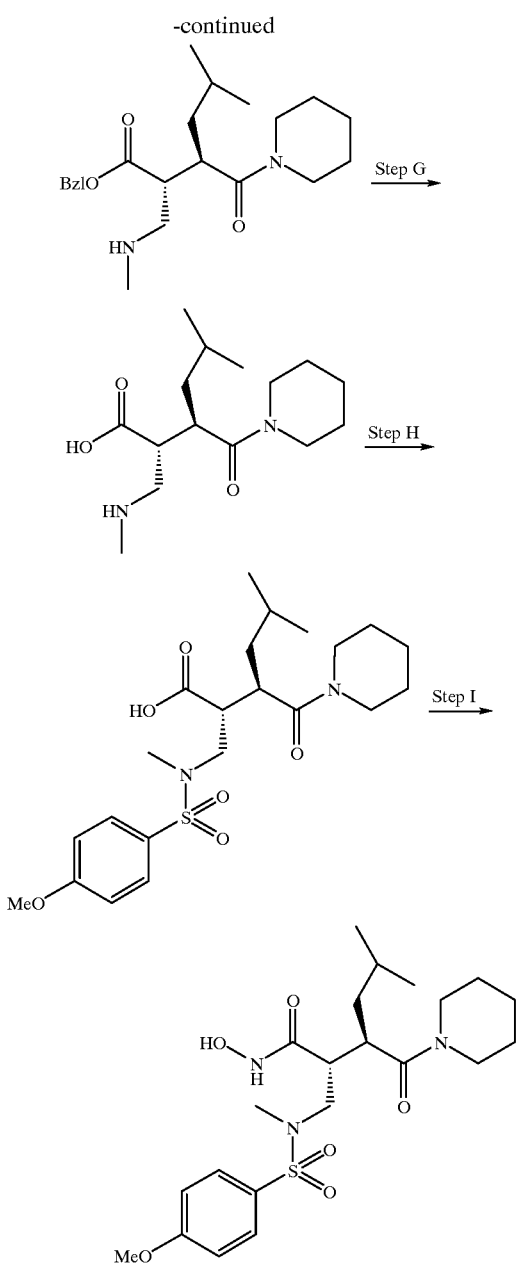

Reagents and conditions: (A) H₂, 10% Pd/C in EtOAc; (B) piperidine aq. HCHO in ethanol; (C) Bzl-Br, K₂CO₃ in acetone; (D) TFA, CH₂Cl₂, 4° C.; (E) pieridine, EDC, HOBt in EtOAc; (F) MeNH₂ in methanol; (G) H₂, 10% Pd/C in ethanol; (H) 4-MeO(C₆H₄)SO₂Cl, Et₃N in THF; (I) HOBt, EDC in DMF, then H₂NOH•HCl, NMM.

Step A: 2-Carboxy-3R-isobutyl-succinic acid 4-tert-butyl ester

2-Benzyloxycarbonyl-3R-carboxy-5-methyl-hexanoic acid 1-benzyl ester 4-tert-butyl ester (55.53 g, 126 mmol) was dissolved in ethyl acetate (500 ml) and subjected to hydrogenolysis in the presence of 10% palladium on charcoal (5.55 g) under conditions similar to those described in Example 1, Step E. After 3 days TLC analysis indicated that deprotection was complete. The catalyst was removed by filtration and the solution was concentrated under reduced pressure to leave the title compound as a clear oil (ca. 33 g, quant.), which was used without further purification. ¹H-NMR: δ (CDCl₃), 3.73 (1H, d, J=9.1 Hz), 3.09 (1H, m), 1.75–1.58 (2H, m), 1.45 (9H, s), 1.31 (1H, m), 0.96 (3H, d, J=6.5 Hz) and 0.92 (3H, d, J=6.5 Hz).

Step B: 3R-Isobutyl-2-methylene-succinic acid 4-tert-butyl ester

2-Carboxy-3R-isobutyl-succinic acid 4-tert-butyl ester (33 g, 126 mmol) was dissolved in ethanol (300 ml) and the solution was cooled in an ice bath during dropwise addition of piperidine (14.95 ml, 151 mmol) followed by 37% aqueous formaldehyde solution (47.17 ml, 630 mmol). The reaction mixture was allowed to warm to room temperature then stirred overnight. The solvent was removed by evaporation and the residue was redissolved in ethyl acetate, washed successively with 1M hydrochloric acid (400 ml) and brine (400 ml), dried over anhydrous sodium sulfate and filtered. The solution was concentrated under reduced pressure to leave the title compound as a colourless oil (28.11 g, 97%). ¹H-NMR: δ (CDCl₃), 6.46 (1H, s), 5.84 (1H, s), 3.50 (1H, t, J=6.3 Hz), 1.85–1.40 (3H, m), 1.45 (9H, s), 0.95 (3H, d, J=6.9 Hz) and 0.93 (3H, d, J=6.9 Hz).

Step C: 3R-Isobutyl-2-methylene-succinic acid 1-benzyl ester 4-tert-butyl ester

3R-Isobutyl-2-methylene-succinic acid 4-tert-butyl ester (28.11 g, 122 mmol) was dissolved in acetone (500 ml) and the solution was placed under an argon atmosphere. Solid potassium carbonate (67.34 g, 488 mmol) was added and the suspension was stirred for 30 minutes. Benzyl bromide (13.13 ml, 110 mmol) was added and the reaction mixture was left to stir overnight at room temperature. The inorganics were removed by filtration and the solvent was removed under reduced pressure to leave the title compound as a yellow oil (35.5 g, ca. 91%; trace benzyl bromide). ¹H-NMR: δ (CDCl₃), 7.45–7.28 (5H, m), 6.37 (1H, s), 5.75 (1H, s), 5.22 (2H, s), 3.55 (1H, t, J=6.9 Hz), 1.75–1.35 (3H, m), 1.40 (9H, s) and 0.90 (6H, t, J=6.5 Hz).

Step D: 3R-Isobutyl-2-methylene-succinic acid 1-benzyl ester

3R-Isobutyl-2-methylene-succinic acid 1-benzyl ester 4-tert-butyl ester (35.5, 111 mmol) was deprotected by TFA acidolysis by the method described previously (Example 1, Step J). After 16 hours the solvents were removed by evaporation under reduced pressure and residual TFA was removed by azeotroping with toluene. The desired product was isolated as a yellow oil (32.5 g, including residual solvent). ¹H-NMR: δ (CDCl₃), 7.42–7.30 (5H, m), 6.45 (1H, s), 5.72 (1H, s), 5.23 (2H, s) 3.68 (1H, t, J=6.9 Hz), 1.90–1.75 (1H, m), 1.70–1.52 (2H, m) and 0.92 (6H, t, J=6.3 Hz).

Step E: 2-[3-Methyl-1R-(piperidine-1-carbonyl)-butyl]-acrylic acid benzyl ester

To a solution of 3R-Isobutyl-2-methylene-succinic acid 1-benzyl ester in ethyl acetate (500 ml) was added HOBt (14.99 g, 111 mmol) followed by EDC (21.31 g, 111 mmol). The solution was stirred for 1 hour at room temperature and piperidine (16.44 ml, 167 mmol) was added slowly. The reaction mixture was stirred for 3 days at room temperature, washed successively with 1 M hydrochloric acid (500 ml), 1M sodium carbonate (500 ml) and brine (300 ml), dried over anhydrous magnesium sulfate and filtered. The filtrate was concentrated to leave an orange oil which was purified by flash chromatography (silica gel, ethyl acetate-hexane, 1:4) to afford the title compound as a yellow oil (19.3 g, 52%). ¹H-NMR: δ (CDCl₃): 7.43–7.30 (5H, m), 6.39 (1H, s), 5.76 (1H, s), 5.22 (2H, s), 4.02 (1H, dd, J=9.4, 5.6 Hz), 3.60–3.30 (4H, m), 1.82 (1H, m), 1.30–1.18 (8H, m) and 0.95–0.85 (6H, m).

Step F: 5-Methyl-2S-methylaminomethyl-3R-(piperidine-1-carbonyl)-hexanoic acid benzyl ester Methylamine (33% in methanol; 6.21 ml, 50 mmol) was added to a stirred solution of 2-[3-Methyl-1R-(piperidine- 1-carbonyl)-butyl]-acrylic acid benzyl ester (8.3 g, 25 mmol) in methanol (50 ml) and the mixture was stirred at room temperature for 90 minutes. The solvent was removed in vacuo to leave the title compound as a yellow oil (15:1 mixture of diastereoisomers by $^1$H-NMR) (8.865 g, 98%). $^1$H-NMR: δ (CDCl$_3$, major diastereoisomer), 7.43–7.28 (5H, m), 5.25–5.12 (2H, m), 3.53–3.50 (4H, m), 3.18 (1H, m), 2.93 (1H, m), 2.71 (1H, d, J=11.9 Hz), 2.63 (1H, dd, J–11.9, 5.0 Hz), 2.35 (3H, s), 1.81–1.30 (9H, m), 1.94 (1H, m) and 0.83–0.75 (6H, m).

Step G: 5-Methyl-2S-methylaminomethyl-3R-(piperid ine-1-carbonyl)-hexanoic acid

The title compound was prepared by hydrogenolysis of the benzyl ester (550 mg, 1.52 mmol) by the method described earlier (Example 1, Step E). The product was isolated as a white amorphous solid (410 mg, 99%). $^1$H-NMR: δ (CD$_3$OD), 3.60–3.40 (6H, m), 3.20–2.95 (2H, m), 2.60 (3H, m), 2.47 (1H, m), 1.80–1.20 (10H, m) and 0.85 (6H, m).

Step H: 2S-{[(4-Methoxybenzenesulfonyl)-methyl-amino]-methyl}-5-methyl-3R-(piperidine-1-carbonyl)-hexanoic acid 5-Methyl-2S-methylaminomethyl-3R-(piperid ine-1-carbonyl)-hexanoic acid (1.51 mmol) was dissolved in dichloromethane (5 ml) and converted to the title sulfonamide by a similar method to that described previously (Example 1, Step I). The solution was washed with 1M hydrochloric acid (25 ml) and brine, dried over anhydrous magnesium sulfate and filtered. The desired product was isolated as a white foam (500 mg, 75%) on removal of the solvent. $^1$H-NMR: δ (CDCl$_3$), 7.75–7.65 (2H, m), 7.05–6.95 (2H, m), 3.88 (3H, m), 3.85–3.38 (6H, m), 3.05–2.80 (2H, m), 2.71 (3H, s), 1.90–1.30 (9H, m) and 1.05–0.85 (6H, m).

Step I: 2S-{[(4-Methoxybenzenesulfonyl)-methyl-amino]-methyl}-5-methyl-3R-(piperidine-1-carbonyl)-hexanoic acid hydroxyamide 2S-{[(4-Methoxybenzenesulfonyl)-methyl-amino]-methyl}-5-methyl-3R-(piperidine-1-carbonyl)-hexanoic acid (500 mg, 1.13 mmol) was converted to the title hydroxamic acid by the procedure described in Example 1. The product was isolated as a white amorphous solid (26 mg, 5%) by flash chromatography (acid-washed silica gel, 3% methanol in dichloromethane). m.p. 147° C. $^1$H-NMR: δ (CD$_3$OD), 7.6 (2H, m), 7.0 (2H, m), 3.78 (3H, s), 3.62–3.02 (7H, m), 2.56 (1H, m), 2.54 (3H, s), 1.59–1.00 (9H, m) and 0.79–0.75 (6H, m). $^{13}$C-NMR: δ (CD$_3$OD), 173.9, 171.2, 164.9, 130.9, 129.0, 115.5, 56.3, 52.3, 48.4, 48.0, 44.3, 42.2, 39.9, 36.7, 27.9, 26.9, 26.9, 25.4, 24.3 and 22.3.

The following additional compound was prepared by analogy with Example 7, substituting the morpholine for piperidine in Step E.

EXAMPLE 8

2S-{[(4-Methoxybenzenesulfonyl)-methyl-amino]-methyl}-5-methyl-3R-(morpholine-1-carbonyl)-hexanoic acid hydroxyamide

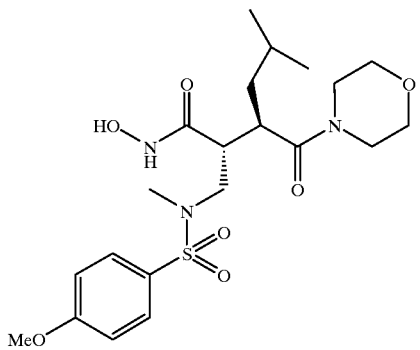

Off-white solid. $^1$H-NMR: δ (CDCl$_3$), 7.67 (2H, d, J=8.7 Hz), 6.98 (2H, d, J=8.8 Hz), 3.77–3.49 (8H, m), 3.44–3.19 (2H, m), 3.01–2.98 (2H, m), 2.62 (3H, s), 1.72 (1H, m), 1.41 (1H, m) and 1.05–0.82 (6H, m). $^{13}$C-NMR: δ (CDCl$_3$), 173.7, 163.0, 129.5, 127.5, 114.3, 76.9, 76.4, 66.6, 55.5, 50.9, 46.7, 44.9, 42.5, 39.9, 37.9, 36.0, 25.7, 23.5 and 21.9.

EXAMPLE 9

2S-[(Methanesulfonyl-methyl-amino)-methyl]-5-methyl-3R-(piperidine-1-carbonyl)-hexanoic acid hydroxyamide

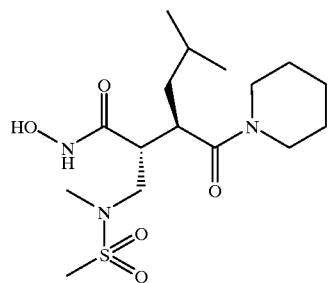

The title compound was prepared according to the route outlined in Scheme 3 and is summarised below.

Scheme 3

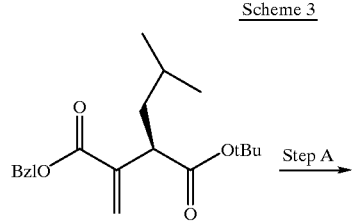

27
-continued

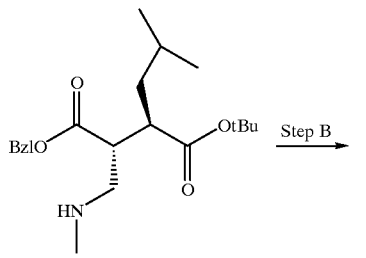 Step B

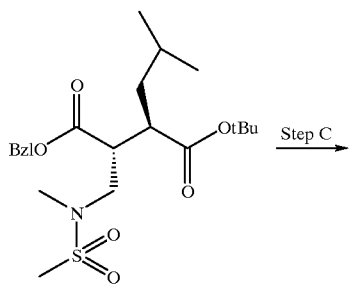 Step C

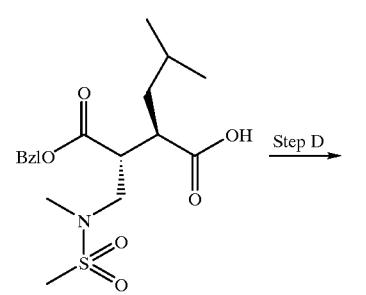 Step D

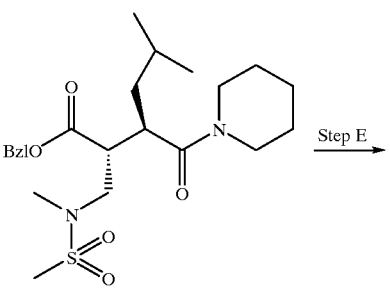 Step E

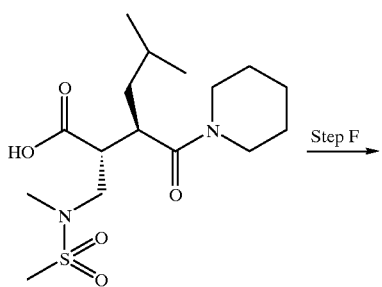 Step F

28
-continued

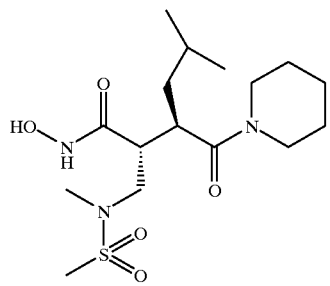

Reagents and conditions: (A) MeNH₂ in methanol; (B) MsCl, Et₃N, CH₂Cl₂; (C) TFA, CH₂Cl₂, 4° C.; (D) piperidine, EDC, HOBt in EtOAc; (E) H₂, 10% Pd/C in EtOAc; (F) HOBt, EDC in DMF, then H₂NOH•HCl, NMM.

Step A: 3-Isobutyl-2-methylaminomethyl-succinic acid 1-benzyl ester 4-tert-butyl ester 3R-Isobutyl-2-methylene-succinic acid 1-benzyl ester 4-tert-butyl ester (Example 7, Step C) (10.0 g, 30.1 mmol) was dissolved in methanol (50 ml) and treated with methylamine (33% in methanol; 7.5 ml, 60.2 mmol) and the reaction mixture was stirred overnight at room temperature. The solvents were removed under reduced pressure to leave the title compound as an oil that was used without further purification. $^1$H-NMR: δ (CDCl$_3$), 7.35 (5H, m), 5.16 (2H, m), 2.95–2.75 (2H, m), 2.74–2.60 (2H, m), 2.48 (3H, s), 1.50 (3H, m), 1.49 (9H, s), 0.97 (1H, m) and 0.80 (6H, d, J=12.5 Hz).

Step B: 3R-Isobutyl-2-[(Methanesulfonyl)-methyl-amino)-methyl]-succinic acid 1-benzyl ester 4-tert-butyl ester 3-Isobutyl-2-methylaminomethyl-succinic acid 1-benzyl ester 4-tert-butyl ester (5.0 g, 13.8 mmol) was dissolved in dichloromethane and the solution was cooled in an ice bath. Triethylamine (3.9 ml, 28 mmol) was added dropwise followed by methanesulfonyl chloride (1.01 ml, 13.1 mmol) and the mixture was stirred at 0° C. for 90 minutes, after which time a thick white precipitate had formed. The mixture was diluted with more dichloromethane (25 ml) and stirred overnight at room temperature. The suspension was washed successively with water, citric acid, sodium hydrogen carbonate and brine, dried over anhydrous magnesium sulfate, filtered and evaporated under reduced pressure to give the desired product (6.10 g, ca. quant.). $^1$H-NMR: δ (CDCl$_3$), 7.40 (5H, m), 5.25, 5.12 (2H, AB system, $J_{AB}$=12.0 Hz), 3.50 (1H, dd, J=13.7, 9.3 Hz), 3.17 (1H, dd, J=13.7, 4.4 Hz), 3.02 (1H, ddd, J=9.3, 9.3, 4.4 Hz), 2.80 (3H, s), 2.70 (3H, s), 2.60 (1H, m), 1.79–1.50 (2H, m), 1.45 (9H, s), 1.00 (1H, m) and 0.80 (6H, d, J=6.5 Hz).

Step C: 3R-Isobutyl-2-[(Methanesulfonyl)-methyl-amino)-methyl]-succinic acid 1-benzyl ester 3R-Isobutyl-2-[(methanesulfonyl)-methyl-amino)-methyl]-succinic acid 1-benzyl ester 4-tert-butyl ester was converted to the title compound by acidolysis with TFA as described previously (Example 1, Step J). $^1$H-NMR: δ (CDCl$_3$), 7.50 (5H, m), 5.20, 5.13 (2H, AB system, $J_{AB}$=12.0 Hz), 3.48 (1H, dd, J=13.5, 9.4 Hz), 3.29 (1H, dd, J=13.6, 5.3 Hz), 3.09 (1H, ddd, J=9.4, 9.4, 5.3 Hz), 2.79 (3H, s), 2.67 (1H, m), 1.60–1.45 (2H, m), 1.08 (1H, m) and 0.82 (6H, d, J=6.4 Hz).

Step D: 2S-[(Methanesulfonyl)-methyl-amino)-methyl]-5-methyl-3R-(piperidine-1-carbonyl)-hexanoic acid benzyl ester 3R-Isobutyl-2-[(methanesulfonyl-amino)-methyl]-succinic acid 1-benzyl ester was coupled with piperidine under standard conditions (see Example 1, Step G). $^1$H-NMR: δ (CDCl$_3$), 7.35 (5H, m), 5.22, 5.14 (2H, AB system J$_{AB}$=12.8 Hz), 3.75–3.35 (6H, m), 3.20–3.00 (3H, m), 2.80 (3H, s), 2.70 (3H, s), 1.85–1.45 (7H, m), 1.08 (1H, m) and 0.80 (6H, m).

Step E: 2S-[(Methanesulfonyl)-methyl-amino)-methyl]-5-methyl-3R-(piperidine-1-carbonyl)-hexanoic acid The title compound was obtained by hydrogenolysis of the benzyl ester (method of Example 1, Step E). $^1$H-NMR: δ (CDCl$_3$), 3.80–3.30 (7H, m), 3.08 (1H, m), 2.90 (3H, s), 2.80 (3H, s), 1.95–1.55 (7H, m), 1.50–1.25 (2H, m) and 1.10–0.85 (6H, m).

Step F: 2S-[(Methanesulfonyl)-methyl-amino)-methyl]-5-methyl-3R-(piperidine-1-carbonyl)-hexanoic acid hydroxyamide Hydroxylamine coupling of 2S-[(Methanesulfonyl)-methyl-amino)-methyl]-5-methyl-3R-(piperidine-1-carbonyl)-hexanoic acid, according to the standard method (Example 1, Step K), gave the title compound as a colourless oil. $^1$H-NMR: δ (CD$_3$OD), 3.61–3.56 (3H, m), 3.54–3.27 (2H, m), 3.12 (1H, m), 2.87 (1H, m), 2.72 (3H, s), 2.69 (3H, s), 2.55 (1H, m), 1.70–1.20 (8H, m), 1.07 (1H, m) and 0.80–0.77 (6H, m). $^{13}$C-NMR: δ (CD$_3$OD), 174.0, 52.0, 48.4, 44.5, 42.0, 40.0, 36.0, 35.0, 28.0, 27.0, 26.5, 26.0, 24.5 and 22.3. IR: v$_{max}$(KBr) 3311, 2930, 1644, 1552,1445, 1328, 1136, 979, 905, 797, 688, 637 and 518 cm$^{-1}$.

The following additional compound was prepared by analogy with Example 9, substituting the appropriate amine for piperidine in Step D.

EXAMPLE 10

2S-[(Methanesulfonyl-methyl-amino)-methyl]-5-methyl-3R-(4-methanesulfonyl-piperazine-1-carbonyl)-hexanoic acid hydroxyamide

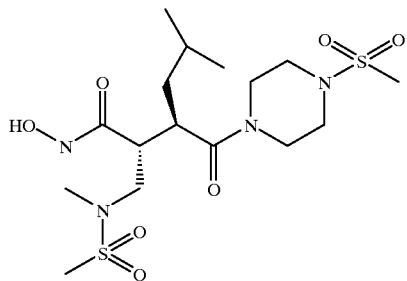

Off-white solid. m.p. 91–94° C. $^1$H-NMR: δ (CD$_3$OD), 3.87–3.66 (4H, m), 3.37–3.14 (9H, m), 2.88 (3H, s), 2.83 (3H, s), 2.78 (3H, s), 1.64 (1H, m), 1.41 (1H, m), 1.28 (1H, m), 0.99–0.86 (6H, m). $^{13}$C-NMR: δ (CD$_3$OD), 175.1,171.5, 52.3, 48.1, 47.4, 47.0, 43.3, 42.7, 36.4, 36.3, 36.1, 27.3, 24.7 and 22.9.

EXAMPLE 11

6-(4-Chlorophenyl)-2-[(methanesulfonyl-methyl-amino)-methyl]-3-(piperidine-1-carbonyl)-hexanoic acid

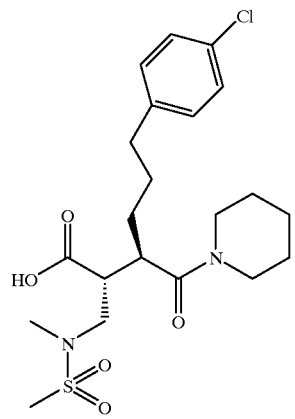

The title compound was prepared from 2-[4-(4-chlorophenyl)-1-(piperidine-1-carbonyl)-butyl]-acrylic acid tert-butyl ester by analogy with Example 9. Red gum. $^1$H-NMR: δ (CD$_3$OD), 7.23 (2H, d, J=8.3 Hz), 7.07 (2H, d, J=8.3 Hz), 3.79–3.40 (6H, m), 3.28 (1H, dd, J=4.1, 15.4 Hz), 2.85 (1H, m), 2.85 (3H, s), 2.84 (3H, s), 2.63–2.52 (2H, m) and 1.79–1.50 (10H, m). $^3$C-NMR: δ (CD$_3$OD), 178.6, 175.8, 144.3, 135.0, 133.5, 131.8, 54.3, 46.8, 44.0, 38.4, 38.0, 37.7, 33.8, 31.9, 30.2, 29.3 and 27.8. IR: v$_{max}$(KBr), 3434, 2941, 1733, 1575, 1333 and 1153 cm$^{-1}$.

The starting material was prepared as follows:
STEP A: 6-(4-Chloro-phenyl)-3-(piperidine-1-carbonyl)-hexanoic acid tert-butyl ester 2[[3-(4-Chlorophenyl)-propyl]-succinic acid 4-tert-butyl ester (WO 95/04033) (5 g, 15.3 mmol) was converted to the corresponding piperidine amide by the method described previously (Example 1, Step G). Yield 4.01 g (67%). $^1$H-NMR: δ (CDCl$_3$), 7.23 (2H, d, J=8.3 Hz), 7.08 (2H, d, J=8.3 Hz), 3.68–3.42 (4H, m), 3.12 (1H, m), 2.69 (1H, dd, J=8.4, 16.4 Hz), 2.62–2.49 (2H, m), 2.29 (1H, dd, J=5.6, 16.4 Hz), 1.72–1.33 (10H, m) and 1.41 (9H, s).

STEP B: 2-[4-(4-Chloro-phenyl)-1-(piperidine-1-carbonyl)-butyl]-malonic acid tert-butyl ester 6-(4-Chloro-phenyl)-3-(piperidine-1-carbonyl)-hexanoic acid tert-butyl ester (2.9 g, 7.4 mmol) was dissolved in THF (80 ml) and the solution was cooled to −78° C. In a separate vessel, diisopropylamine (1.24 ml, 8.8 mmol) was dissolved in THF (30 ml) and cooled to −78° C. before addition of n-butyllithium (2.1M solution in hexane; 3.9 ml, 8.2 mmol). The reaction mixture was allowed to stir for 5 minutes and the LDA thus formed was transferred via a cannula into the first flask. The mixture was stirred for 15 minutes and then transferred via a cannula into a flask containing dry ice pellets under an argon atmosphere. After 2 hours at −78° C. the reaction was allowed to warm slowly to room temperature. The solvents were removed under reduced pressure and the residue was dissolved in ethyl acetate (100 ml). The organic solution was washed successively with 1M hydrochloric acid (40 ml) and water (3×20 ml), dried over anhydrous sodium sulfate, filtered and concentrated to dryness under reduced pressure to a pale yellow foam (3.06 g, 95%) which was used without further purification. $^1$H-NMR: δ (CDCl$_3$), 7.27–7.15 (2H, m), 7.11–7.01 (2H, m), 3.70 (1H, m), 3.60–3.24 (5H, m), 2.65–2.48 (2H, m), 1.87–1.33 (10H, m) and 1.43 (9H, s).
STEP C: 2-[4-(4-Chloro-phenyl)-1-(piperidine-1-carbonyl)-butyl]-acrylic acid tert-butyl ester 2-[4-(4-Chloro-phenyl)-1-(piperidine-1-carbonyl)-butyl]-malonic acid tert-butyl ester (2.0 g, 4.6 mmol) was dissolved in ethanol (100 ml) and treated with piperidine (0.43 ml, 5.5 mmol) and 37% w/w formaldehyde (1.9 ml, 23 mmol). The reaction mixture was heated at 50° C. overnight. The solvent was removed under reduced pressure, the residue was dissolved in ethyl acetate (60 ml), and the solution was washed with water (3×30 ml), dried over anhydrous sodium sulfate, filtered and concentrated under reduced pressure. The residue was purified by column chromatography (silica gel, 20% ethyl acetate in hexane) to give the 2-[4-(4-Chloro-phenyl)-1-(piperidine-1-carbonyl)-butyl]-acrylic acid tert-butyl ester as a colourless oil (750 mg, 41%). $^1$H-NMR: δ (CDCl$_3$), 7.21 (2H, d, J=8.4 Hz), 7.09 (2H, d, J=8.4 Hz), 6.19 (1H, s), 5.71 (1H, s), 3.82 (1H, dd, J=4.9, 8.2 Hz), 3.64 (1H, m), 3.51–3.32 (3H, m), 2.67–2.50 (2H, m), 1.90 (1H, m), 1.61–1.38 (9H, m) and 1.48 (9H, s).

EXAMPLE 12

6-(4-Chlorophenyl)-2-[(methanesufonyl-methyl-amino)-methyl]-3-(piperidine-1-carbonyl)-hexanoic acid hydroxyamide

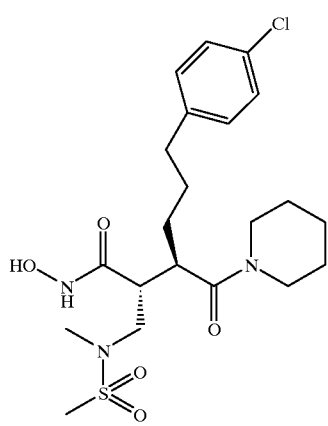

Prepared from 6-(4-chlorophenyl)-2-[(methanesulfonyl-methyl-amino)-methyl]-3-(piperidine-1-carbonyl)-hexanoic acid (Example 11) by direct hydroxylamine coupling (see Example 1, Step K). Pink amorphous solid. $^1$H-NMR: δ (CD$_3$OD), 7.13 (2H, d, J=8.5 Hz), 7.01 (2H, d, J=8.4 Hz), 3.64–3.41 (3H, m), 3.40–3.19 (2H, m),3.02 (1H, m), 2.89 (1H, dd, J=4.6, 13.4 Hz), 2.66 (1H, m), 2.70 (3H, s), 2.69 (3H,s), 2.50–2.39 (2H, m) and 1.61–1.23 (10H, m). $^{13}$C-NMR: δ (CD$_3$OD), 175.7, 173.6, 144.3, 135.0, 133.5, 131.8, 54.4, 50.7, 49.4, 46.7, 44.0, 38.5, 38.3, 38.0, 34.2, 32.0, 30.2, 29.4 and 27.8. IR: ν$_{max}$(KBr) 3211, 2932, 1668, 1615, 1455, 1331 and 1152 cm$^{-1}$.

The following additional compounds were prepared by sulfonylation of 5-Methyl-2S-methylaminomethyl-3R-(piperidine-1-carbonyl)-hexanoic acid benzyl ester (Example 9, Step A) with the appropriate sulfonyl chloride, followed by catalytic transfer hydrogenolysis (4.4% formic acid in methanol, 10% palladium on carbon, room temperature, 4 hours) and direct hydroxylamine coupling. The products were generally isolated in 90–95% purity by preparative reverse phase HPLC.

EXAMPLE 13

2S-{[(4-Butoxybenzenesulfonyl)-methyl-amino]-methyl}-5-methyl-3R-(piperidine-1-carbonyl)-hexanoic acid hydroxyamide

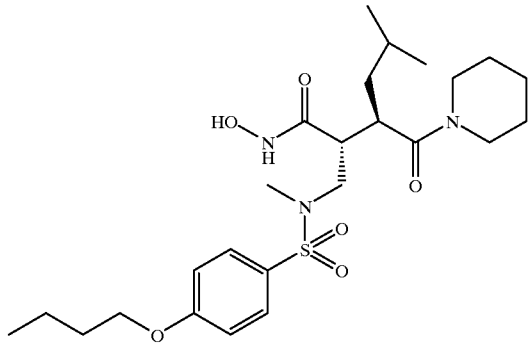

Fluffy white solid. $^1$H-NMR: δ (CD$_3$OD), 7.69 (2H, d, J=4.9 Hz), 7.08 (2H, d, J=5.0 Hz), 4.07 (2H, t, J=6.4 Hz), 3.76–3.53 (3H, br m), 3.51–3.37 (1 H, m), 3.24–3.06 (2H, m), 2.72–2.57 (5H, m), 1.84 (12H, br m), 1.15 (1H, m), 0.99 (3H, t, J=7.3Hz), 0.87 (3H, J=6.5 Hz) and 0.85 (3H, d, J=6.4 Hz).

EXAMPLE 14

2S-{[(2-Cloro-5-trifluoromethyl-benzenesulfonyl)-methyl-amino]-methyl}-5-methyl-3R-(piperidine-1-carbonyl)-hexanoic acid hydroxyamide

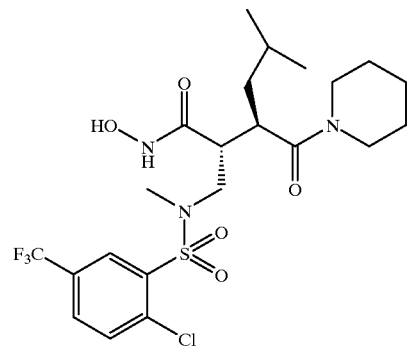

Fluffy white solid. $^1$ H-NMR: δ (CD$_3$OD), 8.25 (H, m), 7.91 (1H, m), 7.82 (1H, m), 3.71–3.39 (5H, br m), 3.11 (2H, m), 2.86 (3H, s), 2.65 (1H, m), 1.72–1.28 (8H, m), 1.12 (1H, m), 0.87 (3H, d, J=6.4 Hz) and 0.85 (3H, d, J=6.5 Hz).

EXAMPLE 15

2S-{[(5-Chloro-1,3-dimethyl-1H-pyrazole-4-sulfonyl)-methyl-amino]-methyl}-5-methyl-3R-(piperidine-1-carbonyl)-hexanoic acid hydroxyamide

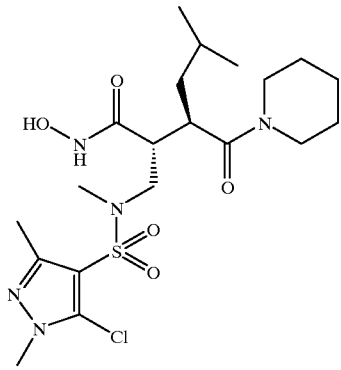

Fluffy, pale pink solid. $^1$H-NMR: δ (CD$_3$OD), 3.82 (3H, s), 3.75–3.54 (3H, m), 3.45 (1H, m), 3.18 (2H, m), 2.96 (1H, m), 2.75 (3H, s), 2.65 (1H, dd, J=4.4, 10.0 Hz), 2.36 (3H, s), 1.74 –1.43 (7H, br m), 1.35 (1H, m), 1.15 (1H, m), 0.88 (3H, d, J=6.4 Hz) and 0.86 (3H, d, J=6.5 Hz).

EXAMPLE 16

2S-{[(4-Chloro-2,5-dimethyl-benzenesulfonyl)-methyl-amino]-methyl}-5-methyl-3R-(piperidine-1-carbonyl)-hexanoic acid hydroxyamide

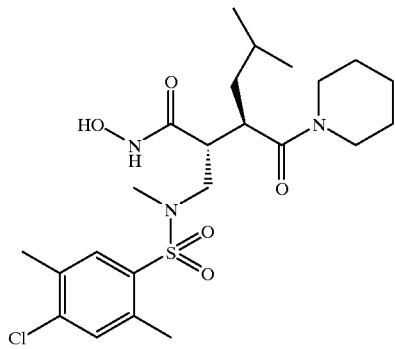

Off white solid. $^1$H-NMR: δ (CD$_3$OD), 7.71 (1H, s), 7.40 (1H, s), 3.74–3.52 (3H, m), 3.46 (1H, m), 3.32(1H, m), 3.12 (1H, dt, J=3.3, 10.5 Hz), 2.86 (1H, m), 2.77 (3H, s), 2.63 (1H, dt, J=3.7, 10.5 Hz), 2.51 (3H, s), 2.40 (3H, s), 1.71–1.26 (8H, br m), 1.01 (1H, m), 0.86 (6H, d, J=6.6 Hz).

EXAMPLE 17

2S-{[(2,5-Dimethoxybenzenesulfonyl)-methyl-amino]-methyl}-5-methyl-3R-(piperidine-1-carbonyl)-hexanoic acid hydroxyamide

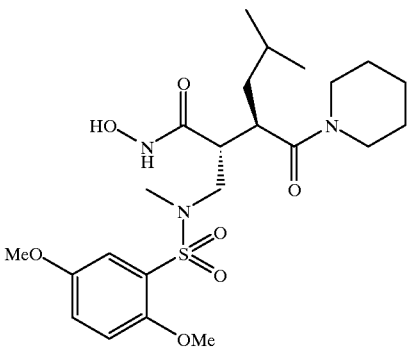

Off white solid. $^1$H-NMR: δ (CD$_3$OD), 7.37 (1H, m), 7.13 (2H, m), 3.86 (3H, s), 3.80 (3H, s), 3.64–3.51 (3H, m), 3.49 (1H, m), 3.26 (1H, m), 3.14 (1H, m), 2.92 (1H, m), 2.77 (3H, s), 2.63 (1H, dt, J=4.2, 10.2 Hz), 1.70–1.26 (8H, br m), 1.12 (1H, m), 0.88 (3H, d, J=6.4 Hz) and 0.86 (3H, d, J=6.5 Hz).

EXAMPLE 18

5-Methyl-2S-{[methyl-(quinoline-8-sulfonyl)-amino]-methyl}-3R-(piperidine-1-carbonyl)-hexanoic acid hydroxyamide

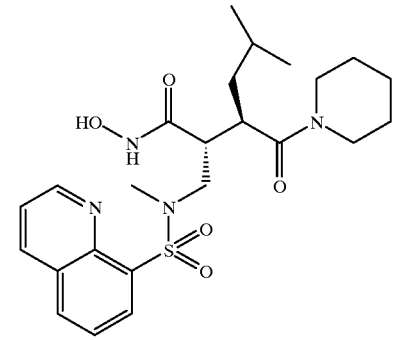

Off white solid. $^1$H-NMR: δ (CD$_3$OD), 9.01 (1H, m), 8.46 (1H, m), 8.42 (1H, m), 8.21 (1H, m), 7.73 (1H, m), 7.65 (1H, m), 3.64–3.40 (5H, br m), 3.17 (2H, m), 2.87 (3H, s), 2.68 (1H, dt, J=4.1, 10.2 Hz), 1.72–1.21 (8H, br m), 1.17 (1H, m), 0.88 (3H, d, J=6.4 Hz) and 0.85 (3H, d, J=6.5 Hz).

EXAMPLE 19

2S-{[(Ethanesulfonyl)-methyl-amino]-methyl}-5-methyl-3R-(piperidine-1-carbonyl)-hexanoic acid hydroxyamide

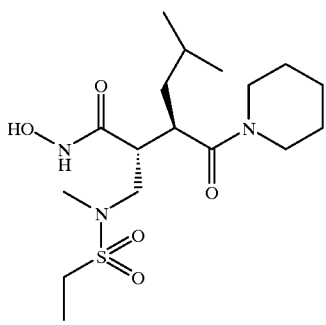

White solid. ¹H-NMR: δ (CD$_3$OD), 3.62 (4H, m), 3.49 (1H, m), 3.17 (1H, dt, J=3.3, 10.4 Hz), 3.06 –2.94 (3H, br m), 2.80 (3H, s), 2.61 (1H, dt, J=4.1, 10.3 Hz), 1.76–1.49 (7H, br m), 1.48 (1H, m), 1.27 (3H, t, J=7.4 Hz), 1.16 (1H, m), 0.89 (3H, d, J=6.4 Hz) and 0.86 (3H, d, J=6.5 Hz).

EXAMPLE 20

2S-{[(4-Chlorobenzenesulfonyl)-methyl-amino]-methyl}-5-methyl-3R-(piperidine-1-carbonyl)-hexanoic acid hydroxyamide

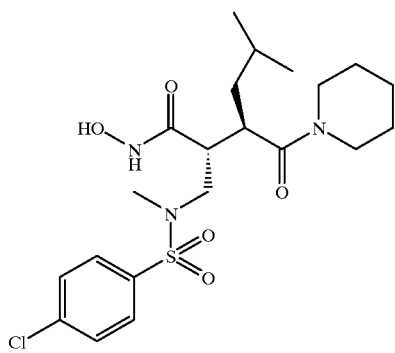

Off white solid. ¹H-NMR: δ (CD$_3$OD), 7.75 (2H, d, J=8.7 Hz), 7.61 (2H, d, J=8.7 Hz), 3.72–3.42 (4H, br m), 3.24–3.08 (2H, br m), 2.70 (2H, m), 2.69 (3H, s), 1.73–1.28 (8H, br m), 1.16 (1H, m), 0.88 (3H, d, J=6.5Hz) and 0.86 (3H, d, J=6.5 Hz).

EXAMPLE 21

5-Methyl-2S-[(methyl-phenylmethanesulfonyl-amino)-methyl]-3R-(piperidine-1-carbonyl)-hexanoic acid hydroxyamide

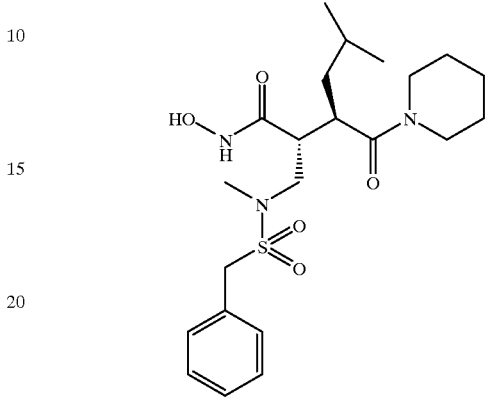

Sticky brown solid. ¹H-NMR: δ (CD$_3$OD), 7.38 (5H, m), 4.81 (2H, s), 3.61 (2H, m), 3.38 (2H, m), 3.19 (1H, dd, J=10.4, 13.6 Hz), 3.04 (1H, dt, J=3.4, 10.5 Hz), 2.78 (3H, s), 2.64 (1 H, dd, J=4.0, 9.3 Hz), 2.52 (1 H, dt, J=4.0, 10.2 Hz), 1.75–1.41 (7H, br m), 1.31 (1H, m), 1.09 (1H, m), 0.84 (6H, d, J=6.6 Hz).

EXAMPLE 22

2S-{[(5-Dimethylamino-naphthalene-1-sulfonyl)-methyl-amino]-methyl}-5-methyl-3R-(piperidine-1-carbonyl)-hexanoic acid hydroxyamide

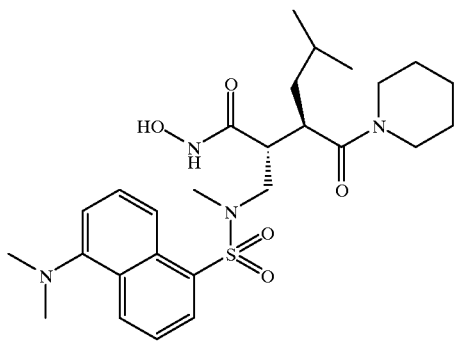

Sticky yellow solid. ¹H-NMR: δ (CD$_3$OD), 8.56 (1H, d, J=8.6 Hz), 8.50 (1H, d, J=8.7 Hz), 8.15 (1H, d, J=6.4 Hz), 7.64 (2H, m), 7.43 (1H, d, J=7.4 Hz), 3.61–3.37 (5H, br m), 3.12 (1H, m), 2.99 (6H, s), 2.82 (1H, m), 2.75 (3H, s), 2.69 (1H, m), 1.82–1.23 (8H, br m), 1.14 (1H, m), 0.86 (3H, d, J=6.4 Hz) and 0.85 (3H, d, J=6.5 Hz).

EXAMPLE 23

5-Methyl-2S-{[methyl-(octane-1-sulfonyl)-amino]-methyl}-3R-(piperidine-1-carbonyl)-hexanoic acid hydroxyamide

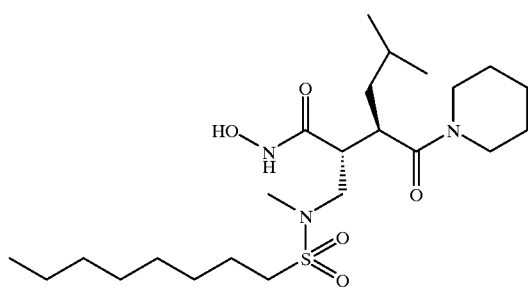

Purple gum. $^1$H-NMR: δ (CD$_3$OD), 3.72–3.54 (4H, br m), 3.46 (1 H, dd, J=10.5, 13.5 Hz), 3.17 (1H, m), 3.04–2.91 (3H, br m), 2.80 (3H, s), 2.60 (1H, dt, J=4.1, 10.2 Hz), 1.80–1.51 (9H, br m), 1.49–1.24 (11H, br m), 1.16 (1H, m) and 0.95–0.82 (9H, br m).

EXAMPLE 24

5-Methyl-2S-{[methyl-(napthalene-2-sulfonyl)-amino]-methyl}-3R-(piperidine-1-carbonyl)-hexanoic acid hydroxyamide

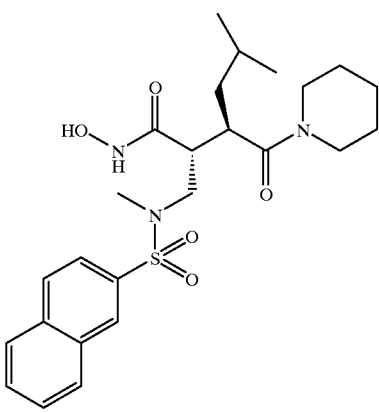

White solid. $^1$H-NMR: δ (CD$_3$OD), 8.38 (1 H, br s), 8.10 (1H, s), 8.06 (1H, s), 8.00 (1H, m), 7.74 (1H, m), 7.68 (2H, m), 3.72–3.42 (4H, br m), 3.31 (1H, m), 3.15 (1H, m), 2.74 (3H, s), 2.80–2.60 (2H, br m), 1.71–1.25 (8H, br m), 1.15 (1H, m), 0.87 (3H, d, J=6.4 Hz) and 0.86 (3H, d, J=6.5 Hz).

EXAMPLE 25

2S-{[(3,4-Dichlorobenzenesulfonyl)-methyl-amino]-methyl}-5-methyl-3R-(piperidine-1-carbonyl)-hexanoic acid hydroxyamide

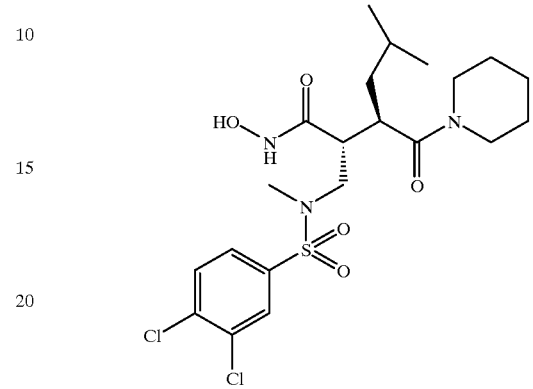

Fluffy white solid. $^1$H-NMR: δ (CD$_3$OD), 7.91 (1H, d, J=2.0 Hz), 7.78 (1H, m), 7.65 (1H, m), 3.77–3.54 (3H, br m), 3.49 (1H, m), 3.28 (1H, m), 3.16 (1H, m), 2.72 (3H, s), 2.69 (2H, m), 1.73–1.28 (8H, br m), 1.17 (1H, m), 0.88 (3H, d, J=6.4 Hz) and 0.86 (3H, d, J=6.5 Hz).

EXAMPLE 26

2S-{[(5-Chloro-2-methoxybenzenesulfonyl)-methyl-amino]-methyl}-5-methyl-3R-(piperidine-1-carbonyl)-hexanoic acid hydroxyamide

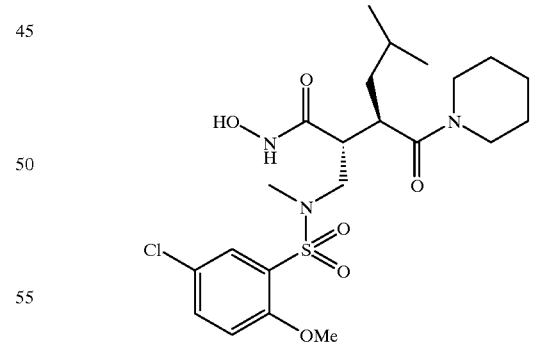

Fluffy white solid. $^1$H-NMR: δ (CD$_3$OD), 7.77 (1 H, d, J=2.7 Hz), 7.58 (1 H, m), 7.20 (1H, d, J=8.9 Hz), 3.92 (3H, s), 3.64–3.50 (4H, br m), 3.29 (1H, m), 3.15 (1H, dd, J=3.3, 10.4 Hz), 2.95 (1H, m), 2.78 (3H, s), 2.63 (1H, m), 1.72–1.29 (8H, br m), 1.14 (1H, m), 0.88 (3H, d, J=6.4 Hz) and 0.85 (3H, d, J=6.5 Hz).

EXAMPLE 27

2S-{[4-(1,1-Dimethylpropyl)-benzenesulfonyl-methyl-amino]-methyl}-5-methyl-3R-(piperidine-1-carbonyl)-hexanoic acid hydroxyamide

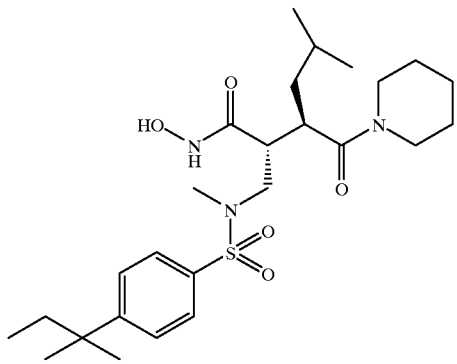

Off white solid. $^1$H-NMR: δ (CD$_3$OD), 7.69 (2H, d, J=8.7 Hz), 7.58 (2H, d, J=8.7 Hz), 3.71 (2H, m), 3.52 (1H, m), 3.41 (1H, m), 3.18 (2H, m), 2.66 (3H, s), 2.65 (2H, m), 1.72 (2H, q, J=7.5 Hz), 1.69–1.46 (7H, br m), 1.35 (1H, m), 1.32 (6H, s), 1.15 (1 H, m), 0.88 (3H, d, J=6.4 Hz), 0.85 (3H, d, J=6.5 Hz) and 0.67 (3H, t, J=7.4 Hz).

EXAMPLE 28

2S-{[(Biphenyl-4-sulfonyl)-methyl-amino}-methyl}-5-methyl-3R-(piperidine-1-carbonyl)-hexanoic acid hydroxyamide

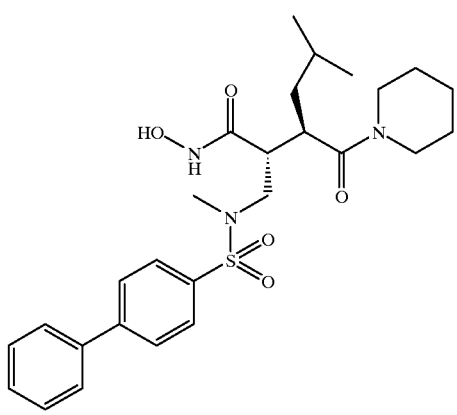

White solid. $^1$H-NMR: δ (CD$_3$OD), 7.85 (4H, m), 7.68 (2H, d, J 6.8 Hz), 7.46 (3H, m), 3.87–3.36 (4H, br m), 3.20 (2H, m), 2.73 (2H, m), 2.72 (3H, s), 1.72–1.27 (8H, br m), 1.17 (1H, m), 0.88 (3H, d, J=6.4 Hz) and 0.85 (3H, d, J=6.5 Hz).

EXAMPLE 29

5-Methyl-3R-(piperidine-1-carbonyl)-2S-{[(trifluoromethanesulfonyl)-methyl-amino]-methyl}-hexanoic acid hydroxyamide

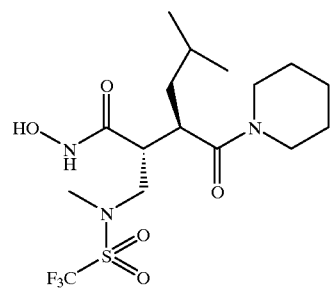

Sticky brown solid. $^1$H-NMR: δ (CD$_3$OD), 3.70–3.49 (6H, br m), 3.18 (1H, dt, J=3.5, 10.3 Hz), 2.99 (3H, s), 2.68 (1H, dt, J=4.1, 10.0 Hz), 1.76–1.49 (7H, br m), 1.39 (1H, m), 1.17 (1H, m), 0.89 (3H, d, J=6.4 Hz) and 0.87 (3H, d, J=6.5 Hz).

EXAMPLE 30

2S-{[(Butanesulfonyl)-methyl-amino]-methyl}-5-methyl-3R-(piperidine-1-carbonyl)-hexanoic acid hydroxyamide

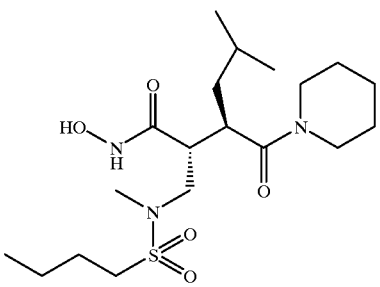

Sticky white solid. $^1$H-NMR: δ (CD$_3$OD), 3.61 (4H, m), 3.47 (1 H, dd, J 10.4, 13.5 Hz), 3.17 (1H, m), 2.95 (3H, m), 2.80 (3H, s), 2.60 (1H, m), 1.79–1.29 (12H, m), 1.15 (1H, m), 0.95 (3H, t, J7.3 Hz), 0.89 (3H, d, J=6.4 Hz) and 0.86 (3H, d, J=6.5 Hz).

EXAMPLE 31

5-Methyl-2S-{[methyl-(toluene-4-sulfonyl)-amino]-methyl]-3R-(piperidine-1-carbonyl)-hexanoic acid hydroxyamide

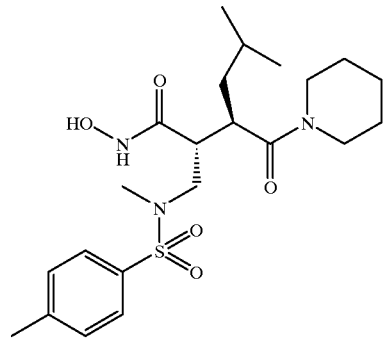

Fluffy white solid. $^1$H-NMR: δ (CD$_3$OD), 7.63 (2H, d, J=8.3 Hz), 7.41 (2H, d, J=8.1 Hz), 3.75–3.65 (3H, m), 3.45 (2H, m), 3.17 (2H, m), 2.66 (1 H, m), 2.64 (3H, s), 2.43 (3H, s), 1.72–1.27 (8H, br m), 1.15 (1H, m), 0.88 (3H, d, J=6.4 Hz) and 0.85 (3H, d, J=6.5 Hz).

The following additional compounds are prepared by the method of Example 9, using 3R-cyclopentylmethyl-2-methylene-succinic acid 1-benzyl ester and the appropriate sulfonyl chloride (Step C).

- 4-cyclopentyl-N-hydroxy-2S-{[(4-methoxybenzenesulfonyl)-methylamino]-methyl}-3R-(piperidine-1-carbonyl)-butyramide
- 4-cyclopentyl-N-hydroxy-2S-{[methyl-(toluene-4-sulfonyl)-amino]-methyl}-3R-(piperidine-1-carbonyl)-butyramide
- 4-cyclopentyl-N-hydroxy-2S-{[(5-Dimethylamino-naphthalene-1-sulfonyl)-methyl-amino]-methyl}-3R-(piperidine-1-carbonyl)-butyramide
- 4-cyclopentyl-N-hydroxy-2S-{[methyl-(naphthalene-2-sulfonyl)-amino]-methyl}-3R-(piperidine-1-carbonyl)-butyramide
- 4-cyclopentyl-N-hydroxy-2S-[(methyl-phenylmethanesulfonyl-amino)-methyl]-3R-(piperidine-1-carbonyl)-butyramide
- 4-cyclopentyl-N-hydroxy-2S-{[(4-butoxybenzenesulfonyl)-methyl-amino]-methyl}-3R-(piperidine-1-carbonyl)-butyramide The starting material 3R-cyclopentylmethyl-2-methylene-succinic acid 1-benzyl ester 4-tert-butyl ester is prepared from 2-benzyloxycarbonyl-3R-carboxy-4-cyclopentyl-butyric acid 1-benzyl ester 4-tert-butyl ester by analogy with Example 7. 2-Benzyloxycarbonyl-3R-carboxy-4-cyclopentyl-butyric acid 1-benzyl ester 4-tert-butyl ester is prepared essentially by literature methods (e.g. M. J. Broadhurst et al, Bioorg Med. Chem. Lett. 1997, 7, 2299–2302).

The following compounds were prepared using the method of Example 9, starting from 3R-isobutyl-2-methylene-succinic acid 1-benzyl ester 4-tert-butyl ester or 3R-cyclopentyl-2-methylene-succinic acid 1-benzyl ester 4-tert-butyl ester and the appropriate amines and sulfonamides. The products were purified by preparative HPLC.

EXAMPLE 32

2S-{[(5-Dimethylaminonaphthalene-1-sulfonyl)-methyl-amino]-methyl}-5-methyl-3R-(morpholine-4-carbonyl)-hexanoic acid hydroxyamide (trifluoroacetic acid salt)

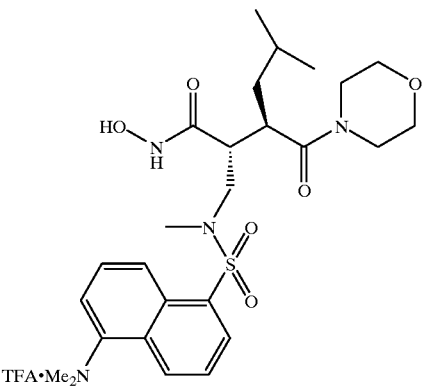

Yellow solid. m.p. 88–94° C. $^1$H-NMR: δ (CD$_3$OD), 8.57 (1H, d, J 9.0 Hz), 8.54 (1H, d, J=8.8 Hz), 8.16 (1H, d, J=7.4 Hz), 7.67 (2H, m), 7.47 (1H, d, J=7.7 Hz), 3.73–3.37 (8H, br m), 3.14–2.82 (3H, m), 3.02 (6H, s), 2.75 (3H, s), 2.69 (1H, m), 1.64 (1H, m), 1.36 (1H, m), 1.18 (1H, m) and 0.86 (6H, d, J=6.5 Hz). $^{13}$C-NMR: δ(CD$_3$OD), 174.8, 171.1, 135.4, 131.9, 131.6, 131.0, 129.7, 125.6, 123.1, 117.9, 68.2, 52.0, 48.3, 46.6, 44.1, 42.5, 40.3, 36.8, 27.4, 24.6 and 22.7. IR: ν$_{max}$ 2959, 2358, 1675, 1614, 1456, 1332, 1140, 1042, 966, 795, 723, 622 and 578 cm$^{-1}$. Found: C 49.68% H 5.93% N 8.23%; C$_{28}$H$_{39}$N$_4$O$_8$SF$_3$. 1.6 H$_2$O requires 49.64% H 6.26% N 8.27%.

EXAMPLE 33

3R-Cyclopentylmethyl-N-hydroxy-2S-[(methanesulfonyl-methyl-amino)-methyl)]-4-oxo-4-piperidin-1-yl-butyramide

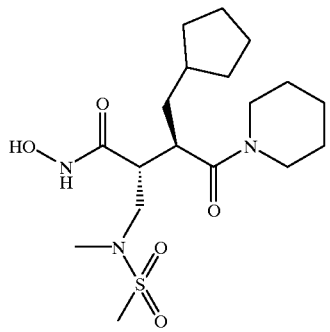

White foam. m.p. 78–80° C. $^1$H-NMR: δ (CD$_3$OD), 3.57 (4H, m), 3.40 (1H, dd, J=10.1, 13.5 Hz), 3.31 (1H, m), 2.97 (1H, dd, J=4.4, 13.5 Hz), 2.82 (3H, s), 2.79 (3H, s), 2.67 (1H, m), 1.55 (14H, br m), 1.35 (1H, m) and 1.10 (2H, m). $^{13}$C-NMR: δ (CD$_3$OD), 174.3, 171.7, 52.1, 48.4, 46.2, 44.8, 41.9, 39.7, 39.2, 36.4, 36.0, 35.4, 34.2, 28.3, 27.3, 26.6 and 25.9. IR: ν$_{max}$(reflection disc) 3193, 2943, 1778, 1713, 1663, 1601, 1449, 1331, 1154, 1022 and 967 cm$^{-1}$. C$_{18}$H$_{33}$N$_3$O$_5$S (403.5); MS (electrospray): 404.4 [M+H]$^+$, 426.2 [M+Na]$^+$.

EXAMPLE 34

3R-Cyclopentylmethyl-N-hydroxy-2S-[(methanesulfonyl-methyl-amino)-methyl)]-4-morpholin-4-yl-4-oxo-butyramide

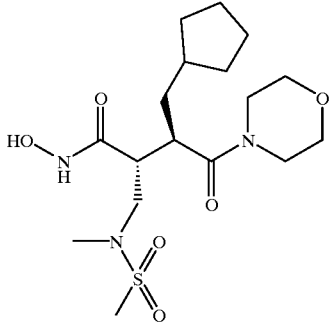

White foam. m.p. 82–84° C. $^1$H-NMR: δ (CD$_3$OD), 3.71 (8H, br m), 3.32 (1H, m), 3.10 (2H, m), 2.82 (3H, s), 2.78 (3H, s), 2.71 (1 H, m), 1.58 (8H, br m), 1.34 (1H, m) and 1.10 (2H, m). $^{13}$C-NMR: δ (CD$_3$OD), 173.2, 169.9, 66.5, 50.5, 46.6, 42.4, 39.7, 38.0, 37.3, 34.3, 33.3, 32.0 and 24.8. IR: V$_{max}$ 3218, 2944, 2870, 1774, 1611, 1451, 1327, 1153, 1036 and 967 cm$^{-1}$.

EXAMPLE 35

3R-Cyclopentylmethyl-N-hydroxy-2S-{[(4-benzenesulfonyl)-methyl-amino]-methyl}-4-oxo-4-piperidine-1-yl-butyramide

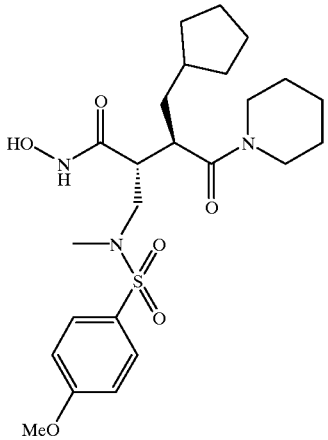

White foam. m.p. 64–65° C. $^1$H-NMR: δ (CD$_3$OD), 7.69 (2H, d, J 8.9 Hz), 7.10 (2H, d, J=8.9 Hz), 3.87 (3H, s), 3.70 (2H, m), 3.47 (2H, m), 3.17 (2H, m), 2.64 (3H, s), 2.61 (2H, m) and 1.76–1.06 (17H, br m). $^{13}$C-NMR: δ (CD$_3$OD), 174.3, 171.6, 165.3, 131.3, 129.4, 115.9, 56.7, 52.8, 48.7, 48.3, 44.7, 41.5, 39.7, 39.1, 37.1, 35.0, 33.7, 28.4, 27.3, 26.6 and 25.8. IR v$_{max}$ 3200, 2942, 2862, 1777, 1598, 1498, 1454, 1343, 1261, 1161 and 1024 cm$^{-1}$.

EXAMPLE 36

3R-Cyclopentylmethyl-N-hydroxy-2S-{[(4-benzenesulfonyl)-methyl-amino]-methyl}-4-morpholin-4-yl-4-oxo-butyramide

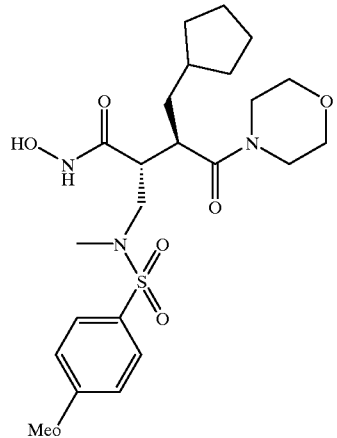

White foam. m.p. 71–72° $^1$H-NMR: δ (CD$_3$OD), 7.70 (2H, d, J=8.9 Hz), 7.11 (2H, d, J=8.9 Hz), 3.88 (3H, s), 3.63 (8H, br m), 3.11 (2H, m), 2.85 (1H, m), 2.72 (1H, m), 2.62 (3H, s) and 1.78–1.09 (11H, br m). $^{13}$C-NMR: δ (CD$_3$OD), 174.9, 171.5, 165.3, 131.3, 129.4, 115.9, 68.2, 56.7, 52.9, 48.1, 44.1, 41.5, 39.7, 39.0, 37.1, 35.0, 33.7 and 26.6. IR: v$_{max}$ 3207, 2950, 1909, 1778, 1603, 1462, 1343, 1264, 1164, 1117, 1027 and 944 cm$^{-1}$.

EXAMPLE 37

2S-[(Methanesulfonyl-methyl-amino)-methyl]-5-methyl-3R-(morpholine-4-carbonyl)-hexanoic acid hydroxyamide

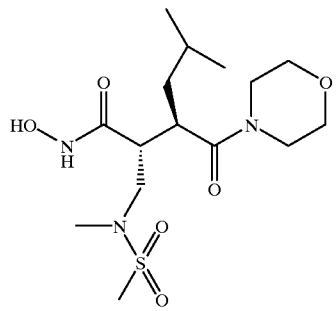

White foam. m.p. 75–78° C. $^1$H-NMR: δ (CD$_3$OD), 3.82–3.62 (8H, m), 3.43–3.35 (1H, m), 3.21–3.10 (2H, m), 2.85 (3H, s), 2.82 (3H, s), 2.75–2.65 (1H, m), 1.74–1.63 (1H, m), 1.50–1.37 (1H, m), 1.29–1.18 (1H, m), 0.92 (3H, d, J=6.4 Hz) and 0.91 (3H, d, J=6.5 Hz). $^{13}$C-NMR: δ (CD$_3$OD), 174.9, 171.5, 68.2, 52.2, 48.3, 44.1, 42.6, 40.3, 36.1, 27.3, 24.7 and 22.7. IR: v$_{max}$ 3224, 2959, 1735, 1614, 1446, 1387, 1328, 1267, 1243, 1153, 1116, 1068, 1040, 965, 782, 575 and 519 cm$^{-1}$.

EXAMPLE 38

2S-{[Ethyl-(4-methoxy-benzenesulfonyl)-amino]-methyl}-5-methyl-3R-(morpholine-4-carbonyl)-hexanoic acid hydroxyamide

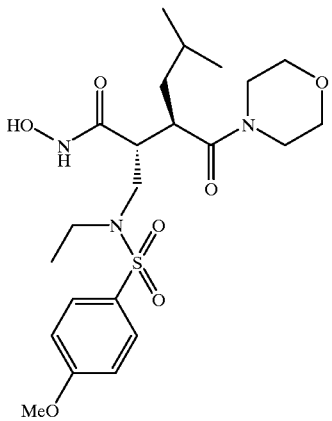

White foam. m.p. 87–89° C. $^1$H-NMR: δ (CDCl$_3$), 10.26 (1H, br s), 7.72 (2H, d, J=8.9 Hz), 6.98 (2H, d, J=8.9 Hz), 3.86 (3H, s), 3.73–3.59 (8H, m), 3.31–3.12 (4H, m), 3.10–2.96 (2H, m), 1.77–1.66 (1H, m), 1.50–1.37 (1H, m), 1.31–1.21 (1H, m), 0.98 (3H, t, J=7.1 Hz), 0.89 (3H, d, J=6.4 Hz) and 0.88 (3H, d, J=6.4 Hz). $^{13}$C-NMR: δ (CDCl$_3$), 174.3, 169.9, 163.5, 130.2, 130.0, 114.8, 67.3, 67.2, 56.0, 48.3, 47.2, 46.2, 45.0, 42.9, 40.1, 37.9, 26.5, 24.0, 22.5 and 13.7. IR: $v_{max}$ 3229, 2959, 1612, 1496, 1463, 1386, 1336, 1303, 1260, 1182, 1154, 1092, 1067, 1024, 892, 838, 804, 730 and 560 cm$^{-1}$. Found: C 53.47% H 7.22% N 8.49%; C$_{22}$H$_{35}$N$_3$O$_7$S. 0.5 H$_2$O requires C 53.42% H 7.34% N 8.50%.

EXAMPLE 39

2S-{[Ethyl-(4-methoxy-benzenesulfonyl)-amino]-methyl}-5-methyl-3R-(piperidine-1-carbonyl)-hexanoic acid hydroxyamide

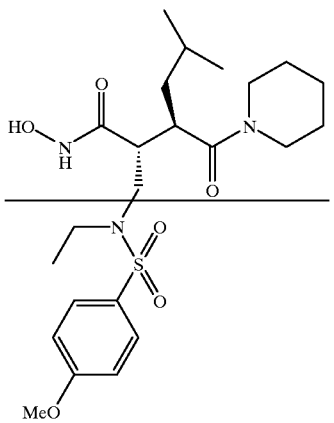

White foam. m.p. 88.5–90° C. $^1$H-NMR: δ (CDCl$_3$), 10.32 (1 H, br s), 7.74 (2H, d, J=8.8 Hz), 6.98 (2H, d, J=8.9 Hz), 3.86 (3H, s), 3.62–3.60 (4H, m), 3.36–3.19 (4H, m), 3.12–2.93 (2H, m), 1.74–1.37 (8H, m), 1.28–1.18 (1H, m), 0.99 (3H, t, J=7.2 Hz), 0.90 (3H, d, J=6.1 Hz) and 0.88 (3H, d, J=6.2 Hz). $^{13}$C-NMR: δ (CDCl$_3$), 175.7, 172.0, 165.2, 132.2, 131.9, 116.5, 57.9, 50.3, 49.6, 47.8, 46.9, 45.5, 41.7, 39.6, 29.0, 28.3, 28.0, 26.7, 25.9, 24.4 and 15.7. IR: $v_{max}$ 3206, 2937, 1597, 1496, 1451, 1336, 1257, 1182, 1153, 1022, 836, 804 and 729 cm$^{-1}$. Found: C 56.41% H 7.69% N 8.54%; C$_{23}$H$_{37}$N$_3$O$_6$S. 0.3 H$_2$O requires C 56.49% H 7.75% N 8.59%.

EXAMPLE 40

3R-Cyclopentylmethyl-2S-{[ethyl-(4-methoxy-benzenesulfonyl)-amino]-methyl}-N-hydroxy-4-oxo-4-morpholine-1-yl-butyramide

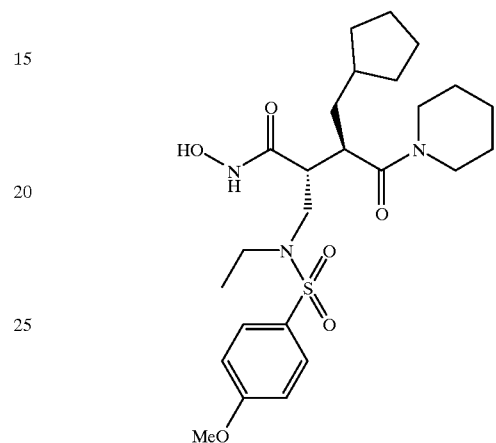

White foam. $^1$H-NMR: δ (CD$_3$OD), 7.74 (2H, d, J=8.9 Hz), 7.06 (2H, d, J=8.9 Hz), 3.87 (3H, s), 3.71 (2H, m), 3.52 (2H, m), 3.30–2.91 (5H, m), 2.72 (1H, m), 1.87–1.38 (14H, m), 1.32 (1H, m) and 1.00 (6H, m). $^{13}$C-NMR: δ (CD$_3$OD), 174.0, 171.4, 164.8, 131.6, 130.7, 115.5, 56.3, 48.0, 45.4, 44.4, 39.4, 38.8, 34.6, 33.4, 28.1, 27.1, 26.2, 25.5 and 13.4. IR: $v_{max}$ 3211, 2948, 1736, 1598, 1497, 1453, 1335, 1261, 1156, 1093 and 1024 cm$^{-1}$. C$_{25}$H$_{39}$N$_3$O$_6$S (509.7); MS (electrospray): 510.4 [M+H]$^+$, 532.2 [M+Na]$^+$.

EXAMPLE 41

3R-Cyclopentylmethyl-2S-{[ethyl-(4-methoxy-benzenesulfonyl)-amino]-methyl}-N-hydroxy-4-morpholine-4-yl-4-oxo-butyramide

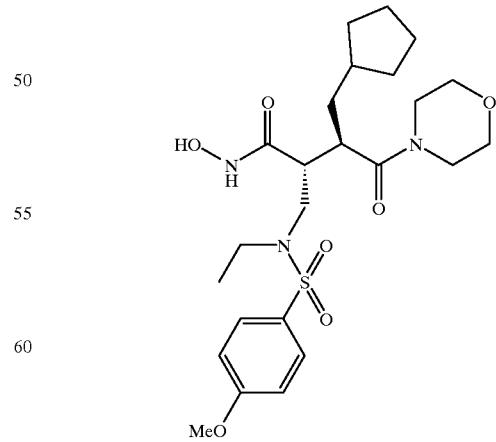

White foam. $^1$H-NMR: δ (CD$_3$OD), 7.72 (2H, d, J 8.9 Hz), 7.08 (2H, d, J=8.9 Hz), 3.87 (3H, s), 3.65 (10H, br m), 3.21 (1H, m), 3.05 (1H, m), 2.89 (1H, m), 2.78 (1H, m), 1.89–1.49 (8H, br m), 1.39 (1H, m), 1.10 (2H, m) and 0.98 (3H, t, J=7.1 Hz). $^{13}$C-NMR: δ (CD$_3$OD), 174.9, 171.6, 165.2, 131.9, 131.6, 115.9, 68.4, 56.7, 48.7, 45.4, 44.2, 39.6, 39.1, 35.0, 33.7, 26.6 and 13.7. IR: $v_{max}$ 3228, 2952, 2862, 1778, 1600, 1497, 1463, 1340, 1263, 1160, 1115 and 1027cm$^{-1}$.

EXAMPLE 42

3R-Cyclopentylmethyl-2S-{[(5-dimethyamino-naphthalene-1-sulfonyl)-methyl-amino]-methyl}-N-hydroxy-4-oxo-4-piperidine-1-yl-butyramide (trifluoroacetic acid salt)

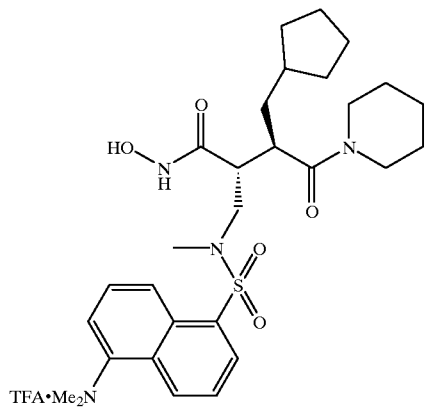

Yellow foam. $^1$H-NMR: δ (CD$_3$OD), 8.57 (1H, d, J=8.6 Hz), 8.51 (1H, d, J=8.7 Hz), 8.14 (1H, d, J=7.4 Hz), 7.65 (2H, m), 7.45 (1H, d, J=7.4 Hz), 3.65 (4H, m), 3.42 (1H, m), 3.08 (1H, m), 3.01 (6H, s), 2.75 (3H, s), 2.71 (2H, m), 1.59 (13H, br m), 1.28 (2H, m) and 1.01 (2H, m). $^{13}$C-NMR: δ (CD$_3$OD), 174.2, 171.5, 150.9, 135.2, 132.0, 131.0, 129.7, 125.5, 123.0, 117.8, 52.1, 48.6, 48.4, 46.6, 44.7, 41.5, 39.6, 39.1, 36.6, 35.0, 33.7, 28.3, 27.3, 26.4 and 22.6. IR: $v_{max}$ 3202, 2944, 1606, 1454, 1332, 1249, 1141, 1048, 1024, 946 and 796 cm$^{-1}$. $C_{29}H_{43}N_4O_5S \cdot C_2F_3O_2$ (558.7); MS (electrospray): 559.4 [M+H]$^+$.

EXAMPLE 43

3R-Cyclopentylmethyl-2S-{[(5-dimethyamino-naphthalene-1-sulfonyl)-methyl-amino]-methyl}-N-hydroxy-4-morpholine-4-yl-4-oxo-butyramide trifluoroacetic acid salt

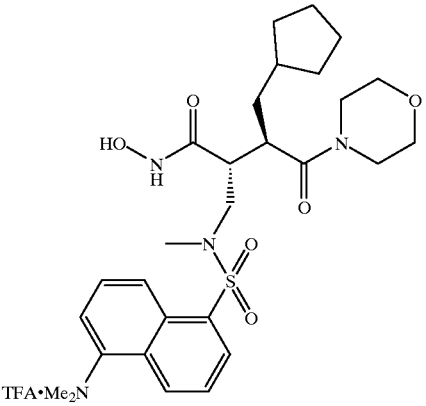

Yellow foam. $^1$H-NMR: δ (CD$_3$OD), 8.56 (1H, d, J=4.5 Hz), 8.54 (1H, d, J=4.6 Hz), 8.14 (1H, d, J=6.3 Hz), 7.68 (2H, m), 7.49 (1H, d, J=7.5 Hz), 3.61 (8H, m), 3.41 (1 H, m), 3.04 (7H, m), 2.91 (1H, m), 2.75 (4H, m), 1.65 (8H, br m), 1.31 (1H, m) and 1.01 (2H, m). $^{13}$C-NMR: δ (CD$_3$OD), 174.8, 171.4, 150.5, 135.2, 132.0, 131.9, 130.9, 129.7, 125.7, 123.3, 118.0, 68.3, 52.1, 48.4, 46.7, 44.1, 41.5, 39.6, 39.0, 36.7, 35.0, 33.7 and 26.6. IR: $v_{max}$ 3207, 2943, 2862, 1636, 1516, 1458, 1333, 1267, 1140, 1042, 946 and 796 cm$^{-1}$. Found C 53.54% H 6.11% N 8.33%. $C_{30}H_{41}F_3N_4O_8S$ requires C 55.35% H 6.44% N 8.33%.

EXAMPLE 44

2S-{[(5-Dimethylaminonaphthalene-1-sulfonyl)-ethyl-amino]-methyl}-5-methyl- 3R-(morpholine-4-carbonyl)-hexanoic acid hydroxyamide (trifluoroacetic acid salt)

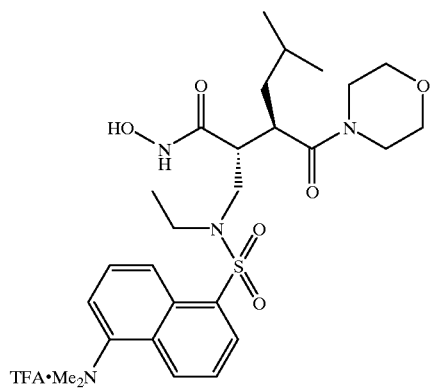

Yellow foam. $^1$H-NMR: δ (CD$_3$OD), 8.60 (1H, d, J=8.5 Hz), 8.40 (1 H, d, J=8.7 Hz), 8.22 (1H, d, J=8.5 Hz), 7.65 (2H, dd, J=8.6, 7.5 Hz), 7.38 (1H, d, J=7.3 Hz), 3.75–3.24 (11 H, m), 3.18–3.00 (2H, m), 2.97 (6H, s), 2.79–2.70 (1 H, m), 1.75–1.64 (1H, m), 1.45–1.32 (1H, m), 1.23–1.13 (1H, m) and 0.91–0.81 (9H, m). $^{13}$C-NMR: δ(CD$_3$OD), 174.7, 171.5, 152.3, 136.6, 131.8, 131.5, 131.4, 129.7, 125.2, 122.0, 117.4, 68.3, 48.8, 46.4, 44.2, 44.0, 42.3, 40.5, 27.4, 24.6, 22.6 and 13.2. IR: $v_{max}$ 3194, 2955, 1609, 1458, 1319, 1267, 1198, 1139, 1042, 932, 892, 794, 717 cm$^{-1}$.

EXAMPLE 45

2S-{[(5-Dimethylaminonaphthalene-1-sulfonyl)-methyl-amino]-methyl}-5-methyl-3R-(piperidine-1-carbonyl)-hexanoic acid hydroxyamide (trifluoroacetic acid salt)

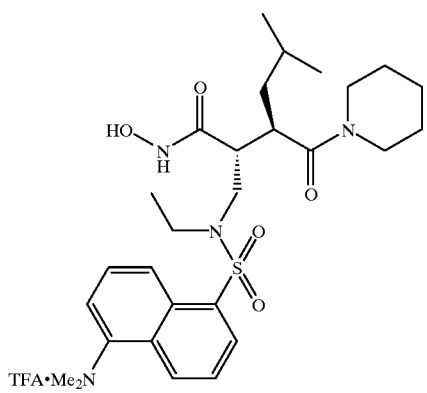

Yellow foam. $^1$H-NMR: δ (CD$_3$OD), 8.60 (1H, d, J=8.5 Hz), 8.39 (1H, d, J=8.7 Hz), 8.22 (1H, d, J=8.5 Hz), 7.67–7.61 (2H, m), 7.38 (1H, d, J=7.5 Hz), 3.75–341 (6H, m), 3.31–3.03 (3H, m), 2.96 (6H, s), 2.77–2.67 (1H, m), 1.73–1.33 (8H, m), 1.21–1.10 (1H, m) and 0.90–0.83 (9H, m). $^{13}$C-NMR: δ (CD$_3$OD), 174.2, 171.6, 136.6, 131.8, 131.5, 129.6, 125.2, 117.3, 111.4, 44.0, 42.4, 41.5, 40.0, 26.0, 25.1, 23.5, 22.3, 20.3 and 10.8. IR: $v_{max}$ 3359, 3360, 3198, 2938, 1777, 1642, 1606, 1465, 1389, 1322, 1251, 1227, 1199, 1140, 1056, 1019, 989, 931 cm$^{-1}$. Found: C 58.55% H 7.62% N 9.69%; C$_{30}$H$_{42}$N$_4$O$_7$SF$_3$. 1.5 H$_2$O requires C 58.62% H 7.91% N 9.76%.

The following additional compounds were prepared from 2-[2-cyclopentyl- 1R-(piperidine-1-carbonyl)-ethyl]-acrylic acid benzyl ester by parallel synthesis in solution using the method of Example 7. Briefly, Michael addition of the appropriate amine was followed by sulfonylation with the desired sulfonyl chloride, catalytic transfer hydrogenolysis (4.4% formic acid in methanol, 10% palladium on carbon, room temperature, 4 hours) and direct hydroxylamine coupling. The products were generally isolated in 90–95% purity by preparative reverse phase HPLC and characterised by electrospray mass spectrometry.

EXAMPLE 46

3R-Cyclopentylmethyl-2S-[(ethanesulfonyl-methyl-amino)-methyl]-N-hydroxy-4-oxo-4-piperidin-1-yl-butyramide

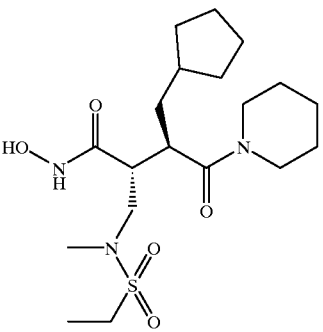

C$_{20}$H$_{37}$N$_3$O$_4$S (415.6); MS (electrospray): 416.6 [M+H]$^+$, 438.6 [M+Na]$^+$.

EXAMPLE 47

3R-Cyclopentylmethyl-N-hydroxy-2S-{[methyl-(propane-2-sulfonyl)-amino]-methyl}-4-oxo-4-piperidin-1-yl-butyramide

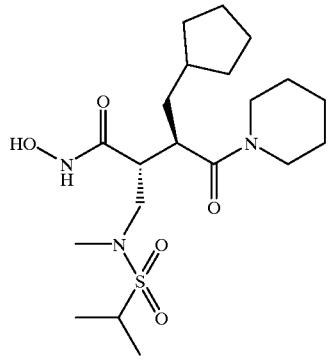

C$_{21}$H$_{39}$N$_3$O$_4$S (429.6); MS (electrospray): 430.6 [M+H]$^+$, 452.6 [M+Na]$^+$.

EXAMPLE 48

3R-Cyclopentylmethyl-N-hydroxy-2S-{[methyl-(octane-1-sulfonyl)-amino]-methyl}-4-oxo-4-piperidin-1-yl-butyramide

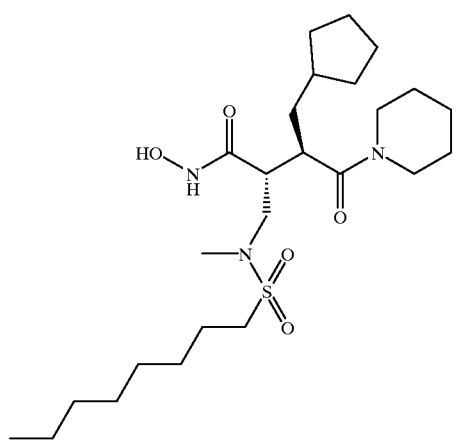

$C_{26}H_{49}N_3O_4S$ (499.8): MS (electrospray): 500.8 [M+H]$^+$, 522.8 [M+Na]$^+$.

EXAMPLE 49

3R-Cyclopentylmenthyl-N-hydroxy-2S-[(methyl-trifluoromethanesulfonyl-amino)-methyl]-4-oxo-4-piperidin-1-yl-butyramide

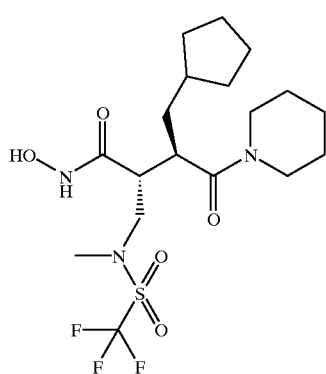

$C_{19}H_{32}F_3N_3O_4S$ (455.5); MS (electrospray): 456.5 [M+H]$^+$, 478.5 [M+Na]$^+$.

EXAMPLE 50

2S-{[(4-Chloro-benzenesulfonyl)-methyl-amino] methyl]-3R-cyclopentylmethyl-N-hydroxy-4-oxo-4-piperidin-1-yl-butyramide

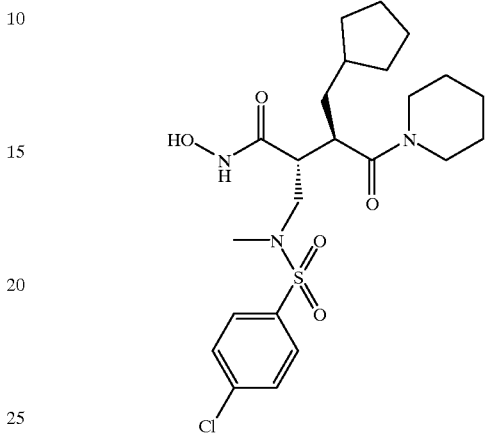

$C_{24}H_{36}ClN_3O_4S$ (498.1); MS (electrospray): 499.1, 501.1 [M+H]$^+$, 521.1, 523.1 [M+Na]$^+$.

EXAMPLE 51

3R-Cyclopentylmethyl-N-hydroxy-2S-{[methyl-(quinoline-8-sulfonyl)-amino]-methyl}-4-oxo-4-piperidin-1-yl-butyramide

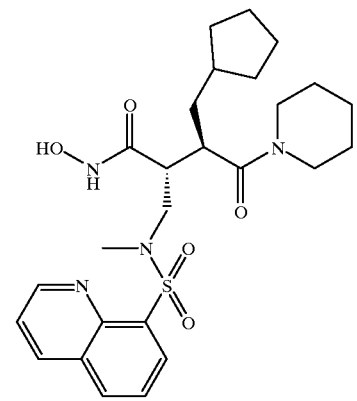

$C_{27}H_{38}N_4O_4S$ (514.7); MS (electrospray): 515.7 [M+H]$^+$, 537.7 [M+Na]$^+$.

EXAMPLE 52

3R-Cyclopentylmethyl-N-hydroxy-2S-{[methyl-(naphthalene-1-sulfonyl)-amino]-methyl}-4-oxo-4-piperidin-1-yl-butyramide

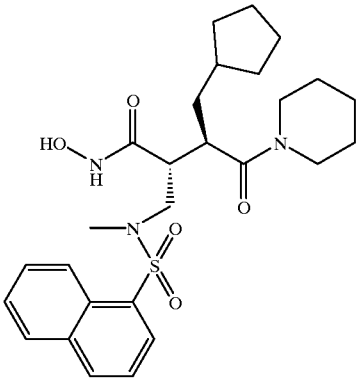

$C_{28}H_{39}N_3O_4S$ (513.7); MS (electrospray): 514.7 [M+H]$^+$, 536.7 [M+Na]$^+$.

EXAMPLE 53

3R-Cyclopentylmethyl-N-hydroxy-2S-{[(isoquinoline-5-sulfonyl)-methyl-amino]-methyl}-4-oxo-4-piperidin-1-yl-butyramide

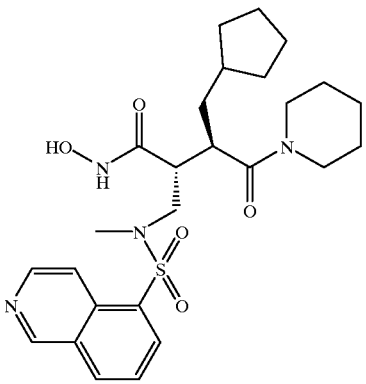

$C_{27}H_{38}N_4O_4S$ (514.7); MS (electrospray): 515.7 [M+H]$^+$, 537.7 [M+Na]$^+$.

EXAMPLE 54

3R-Cyclopentylmethyl-2S-{[(6-dimethylamino-naphthalene-1-sulfonyl)-methyl-amino]-methyl}-N-hydroxy-4-oxo-4-piperidin-1-yl-butyramide

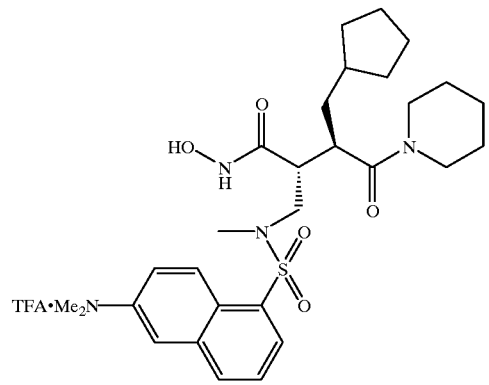

$C_{30}H_{45}N_4O_4S \cdot C_2F_3O_2$ (556.8); MS (electrospray): 557.8 [M+H]$^+$.

EXAMPLE 55

3R-Cyclopentylmethyl-2S-{[dimethylsulfamoyl-methyl-amino]-methyl]-N-hydroxy-4-oxo-4-piperidin-1-yl-butyramide

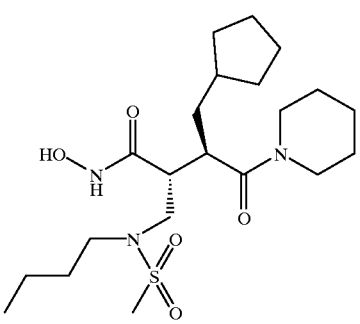

$C_{20}H_{38}N_4O_4S$ (430.6); MS (electrospray): 431.6 [M+H]$^+$, 453.6 [M+Na]$^+$.

EXAMPLE 56

2S-[(Butyl-methanesulfonyl-amino)-methyl]-3R-cyclopentylmethyl-N-hydroxy-4-oxo-4-piperidin-1-yl-butyramide $C_{22}H_{41}N_3O_4S$ (443.7); MS (electrospray): 444.7 [M+H]$^+$, 466.7 [M+Na]$^+$.

EXAMPLE 57

3R-Cyclopentylmethyl-N-hydroxy-2S-[(isopropyl-methanesulfonyl)-amino)-methyl]-4-oxo-4-piperidin-1-yl-butyramide

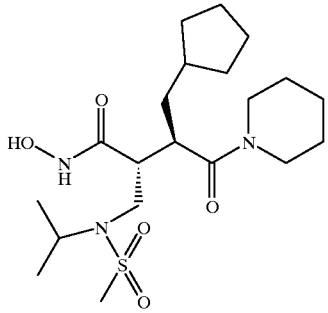

$C_{21}H_{39}N_3O_4S$ (429.6); MS (electrospray): 430.6 [M+H]$^+$, 452.6 [M+Na]$^+$.

EXAMPLE 58

2-S-[(tert-Butyl-methanesulfonyl)-amino)-methyl]-3R-cyclopentymethyl-N-hydroxy-4-oxo-4-piperidin-1-yl-butyramide

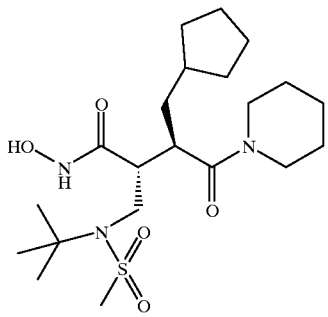

$C_{22}H_{41}N_3O_4S$ (443.7); MS (electrospray): 444.7 [M+H]$^+$, 466.7 [M+Na]$^+$.

EXAMPLE 59

3R-Cyclopentylmethyl-N-hydroxy-2S-[(cyclopropyl-methanesulfonyl)-amino)-methyl]-4-oxo-4-piperidin-1-yl-butyramide

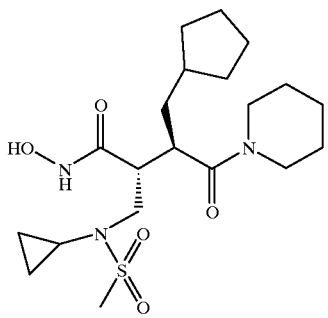

$C_{21}H_{37}N_3O_4S$ (427.6); MS (electrospray): 428.6 [M+H]$^+$, 450.6 [M+Na]$^+$.

EXAMPLE 60

2S-[(Cyclopentyl-methanesulfonyl)-amino)-methyl]-3R-cyclopentylmethyl-N-hydroxy-4-oxo-4-piperidin-1-yl-butyramide

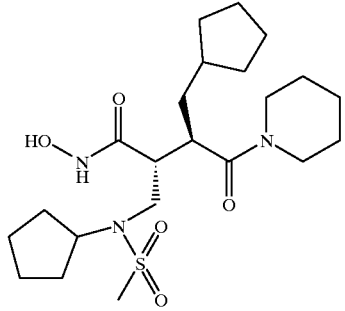

$C_{23}H_{41}N_3O_4S$ (455.7); MS (electrospray): 456.7 [M+H]$^+$, 478.7 [M+Na]$^+$.

BIOLOGICAL EXAMPLE A

The potency of compounds of the present invention as inhibitors of human fibroblast collagenase may be determined by the procedure of Cawston and Barrett, (*Anal. Biochem.*, 99, 340–345, 1979), hereby incorporated by reference, whereby a 1 mM solution of the compound being tested, or a dilution thereof, was incubated at 37° C. for 16 hours with collagen and human fibroblast collagenase (buffered with 25 mM Hepes, pH 7.5 containing 5 mM CaCl$_2$, 0.05% Brij 35 and 0.02% NaN$_3$). The collagen was acetylated $^{14}$C collagen prepared by the method of Cawston and Murphy, (*Methods in Enzymology*, 80, 711, 1981), hereby incorporated by reference. The samples were centrifuged to sediment undigested collagen, and an aliquot of the radioactive supernatant removed for assay on a scintillation counter as a measure of hydrolysis. The collagenase activity in the presence of 1 mM of the test compound, or a dilution thereof, was compared to activity in a control devoid of inhibitor and the result reported below as that of inhibitor concentration effecting 50% inhibition of the collagenase activity (IC$_{50}$). Compounds of the invention tested in this assay were shown to be active as inhibitors of human fibroblast collagenase. For example, in this assay, the compound of Example 2 was shown to have IC$_{50}$ of about 50 nM.

We claim:

1. A compound of formula (I)

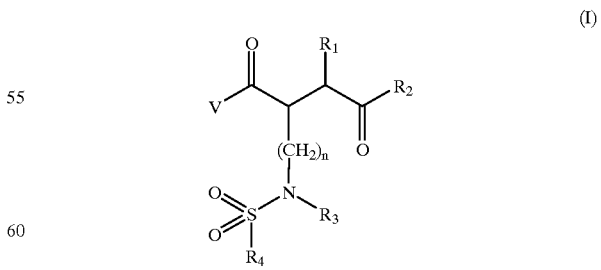

wherein

V is HO— or HONH— n is 1, 2, 3 or 4;

R$_1$ is a C$_1$–C$_{12}$ alkyl, $C_2$–$C_{12}$ alkenyl,
$C_2$–$C_{12}$ alkynyl,
perfluoroalkyl,
phenyl($C_1$–$C_6$ alkyl)-,
heteroaryl($C_1$–$C_6$ alkyl)-,
non-aryl heterocyclyl($C_1$–$C_6$ alkyl)-,
cycloalkyl($C_1$–$C_6$ alkyl)-,
cycloalkenyl($C_1$–$C_6$ alkyl)-,
phenoxy($C_1$–$C_6$ alkyl)-,
heteroaryloxy($C_1$–$C_6$ alkyl)-,
phenyl($C_1$–$C_6$ alkyl)O($C_1$–$C_6$ alkyl)-,
heteroaryl($C_1$–$C_6$ alkyl)O($C_1$–$C_6$ alkyl)-,
phenyl($C_1$–$C_6$ alkyl)S($C_1$–$C_6$ alkyl)- or
heteroaryl($C_1$–$C_6$ alkyl)S($C_1$–$C_6$ alkyl)- group,
any one of which may be optionally substituted by $C_1$–$C_6$ alkyl, trifluoromethyl, $C_1$–$C_6$ alkoxy, hydroxy, halo, cyano (—CN), phenyl, substituted phenyl or heteroaryl;

$R_2$ is a saturated 5- to 8-membered monocyclic N-heterocyclic ring which is attached via the N atom and which, (i) optionally contains as a ring member O, S, SO, $SO_2$, or $NR_5$ wherein $R_5$ is hydrogen, hydroxy, $C_1$–$C_6$ alkyl, ($C_1$–$C_6$ alkoxy)$C_1$–$C_6$ alkyl, benzyl, acyl, an amino protecting group, or a group —$SO_2R_6$ wherein $R_6$ is $C_1$–$C_6$ alkyl or a substituted or unsubstituted phenyl or heteroaryl group, and/or (ii) is optionally substituted on one or more C atoms by hydroxy, $C_1$–$C_6$ alkyl, $C_1$–$C_6$ alkoxy, cyano, oxo, ketalised oxo, amino, mono($C_1$–$C_6$ alkyl)amino, di($C_1$–$C_6$ alkyl)amino, carboxy, $C_1$–$C_6$ alkoxycarbonyl, hydroxymethyl, $C_1$–$C_6$ alkoxymethyl, carbamoyl, mono($C_1$–$C_6$ alkyl)carbamoyl, di($C_1$–$C_6$ alkyl) carbamoyl, or hydroxyimino;

$R_3$ is hydrogen, $C_1$–$C_6$ alkyl, $C_3$–$C_8$ cycloalkyl, or acetyl; and $R_4$ is optionally substituted
$C_1$–$C_6$ alkyl,
$C_2$–$C_6$ alkenyl,
$C_2$–$C_6$ alkynyl,
$C_1$–$C_3$ perfluoroalkyl,
cycloalkyl,
cycloalkyl($C_1$–$C_6$ alkyl)-,
cycloalkenyl,
cycloalkenyl($C_1$–$C_6$ alkyl)-,
di-($C_1$–$C_6$ alkyl)amino,
phenyl,
phenyl($C_1$–$C_6$ alkyl)-,
biphenyl,
phenyl-heteroaryl,
naphthyl,
non-aryl heterocyclyl,
non-aryl heterocyclyl($C_1$–$C_6$ alkyl)-,
heteroaryl or
heteroaryl($C_1$–$C_6$ alkyl)-;
heteroaryl-phenyl;
heteroaryl-heteroaryl;
aryloxyaryl;
or a pharmaceutically acceptable salt hydrate or solvate thereof.

2. A compound as claimed in claim 1 wherein the C atom carrying the $R_1$ group has the R stereoconfiguration, and the C atom carrying the —(C═O)V group has the S stereoconfiguration.

3. A compound as claimed in claim 1 or claim 2 wherein n is 1.

4. A compound as claimed in claim 1 wherein V is HONH—.

5. A compound as claimed in claim 1 wherein $R_1$ is optionally substituted $C_1$–$C_{12}$ alkyl or $C_3$–$C_6$ alkenyl; cycloalkyl($C_1$–$C_6$ alkyl);
phenyl($C_1$–$C_6$ alkyl)- or phenoxy($C_1$–$C_6$ alkyl), either of which may be optionally substituted in the phenyl ring by halogen, $C_1$–$C_6$ alkyl, $C_1$–$C_6$ alkoxy or phenyl.

6. A compound as claimed in claim 5 wherein $R_1$ is n-propyl, isopropyl, n-butyl, iso-butyl, n-pentyl, n-hexyl, n-heptyl, n-octyl, n-nonyl, n-decyl, cyclopropylmethyl, cyclobutylmethyl, cyclopentylmethyl, cyclohexylmethyl, cyclobutylethyl, 1,1,1-trifluoropropyl, phenylpropyl, 4-chlorophenylpropyl, 4-methylphenylpropyl, 4-methoxyphenylpropyl, 4-phenylphenylpropyl, 4-(4-chlorophenyl)phenylpropyl or phenoxybutyl.

7. A compound as claimed in claim 1 wherein $R_2$ is substituted or unsubstituted 1-pyrrolidinyl, piperidino, 1-piperazinyl, hexahydro-1-pyridazinyl, morpholino, tetrahydro-1,4-thiazin-4-yl, tetrahydro-1,4-thiazin-4-yl 1-oxide, tetrahydro-1,4-thiazin-4-yl 1,1-dioxide, thiazolidin-3-yl, hexahydroazipino, or octahydroazocino.

8. A compound as claimed in claim 1 wherein $R_2$ is piperidin-1-yl.

9. A compound as claimed in claim 1 wherein $R_3$ is hydrogen, methyl, ethyl, n- or iso-propyl, n-, sec- or tert-butyl, n-pentyl, n-hexyl, or acetyl.

10. A compound as claimed in claim 1 wherein $R_3$ is hydrogen, acetyl or methyl.

11. A compound as claimed in claim 1 wherein $R_4$ is substituted or unsubstituted methyl, ethyl, n- or iso-propyl, n-, sec- or tert-butyl, n-pentyl, n-hexyl, n-heptyl, n-octyl, cyclopropyl, cyclobutyl, cyclopentyl, cyclohexyl, cycloheptyl, cyclooctyl, cyclopentenyl, cyclohexenyl, cycloheptenyl, cyclooctenyl, phenyl, biphenyl, naphth-1-yl, naphth-2-yl, benzyl, thien-2-yl, furan-2-yl, pyrrolyl, imidazol-2-yl, benzimidazolyl, thiazol-2-yl, benzothiazol-2-yl, pyrazolyl, isoxazol-5-yl, isothiazolyl, triazolyl, thiadiazol-5-yl, oxadiazol-5-yl, pyridin-2-yl, pyridin-3-yl, pyridin-4-yl, N-oxides of pyridin-2-yl, pyridin-3-yl and pyridin-4-yl, quinolinyl, 1,2-pyridazin-3-yl, 1,3-pyrimidin-5-yl, pyrazin-2-yl, triazinyl, piperazin-1-yl, indol-2-yl, benzimidazol-2-yl, benzotriazol-2-yl, 1,3-dithian-2-yl, and benzothien-2-yl, or quinolin-3-yl.

12. A compound as claimed in claim 11 wherein $R_4$ is 2-methoxyphenyl, 3-methoxyphenyl, 4-methoxyphenyl, 4-(n-butoxy)phenyl, 3,4-dimethoxyphenyl, 2,5-dimethoxyphenyl, 2-fluorophenyl, 3-fluorophenyl, 4-fluorophenyl, 2-chlorophenyl, 3-chlorophenyl, 4-chlorophenyl, 3,4-dichlorophenyl, 3,5-dichlorophenyl, 2-chloro-5-trifluoromethyphenyl, 2-bromophenyl, 3-bromophenyl, 4-bromophenyl, 2-iodophenyl, 3-iodophenyl, 4-iodophenyl, 2-methylphenyl, 3-methylphenyl, 4-methylphenyl, 3,4-dimethyl, 2,5-dimethyl-4-chlorophenyl, 2-methoxy-5-chlorophenyl, 2-t-butylphenyl, 3-t-butylphenyl, 4-t-butylphenyl, 4-t-butyl-2,6-dimethylphenyl, 4-(1,1-dimethylpropyl)phenyl, 4-phenylphenyl, 4-(4-chlorophenyl)phenyl, 4-(pyridin-4-yl)phenyl, 2-nitrophenyl, 3-nitrophenyl, 4-nitrophenyl, 2-cyanophenyl, 3-cyanophenyl, 4-cyanophenyl, 2-acetylphenyl, 3-acetylphenyl, 4-acetylphenyl, 2-methylsulfonylphenyl, 3-methylsulfonylphenyl, 4-methylsulfonylphenyl, 2-trifluoromethylphenyl, 3-trifluoromethylphenyl, 4-trifluoromethylphenyl, 3,5-ditrifluoromethylphenyl, 2-aminophenyl, 3-aminophenyl, 4-aminophenyl, 2-N,N-dimethylaminophenyl, 3-N,N-dimethylaminophenyl, 4-N,N-dimethylaminophenyl, 2-hydroxyphenyl, 3-hydroxyphenyl, 4-hydroxyphenyl, 6-dimethylaminonaphth-1-yl; $N^1$-methyl-3-methyl-5- chloroimidazol-4-yl, 4-ethoxycarbonylmethyl-thiazol-2-yl, 4-phenylthiazol-2-yl, 4,5-dimethylthiazol-2-yl, 5-bromothiazol-2-yl, 4-tert-butylthiazol-2-yl, 1,2,4-oxadiazol-5-yl, 3-methyl-1,2,4-oxadiazol-5-yl, 3-phenyl-1,2,4-oxadiazol-5-yl, 1,2,4-oxadiazol-3-yl, 1,3,4-oxadiazol-2-yl, 1,2,4-thiadiazol-5-yl, 3-phenyl-1,2,4-thiadiazol-5-yl, 1,3,4-thiadiazol-2-yl, or 5-methyl-1,3,4-thiadiazol-2-yl.

13. A compound as claimed in claim 11 wherein $R_4$ is methyl, ethyl, n-butyl, n-octyl, dimethylamino, trifluoromethyl, phenyl, 4-methoxyphenyl, 4-butoxyphenyl, 2,5-dimethoxyphenyl, 4-chlorophenyl, 3,4-dichlorophenyl, 2-chloro-5-methoxyphenyl, 2-chloro-5-trifluoromethylphenyl, 5-chloro-1,3-dimethyl-phenyl-, 5-chloro-1,3-dimethyl-1H-pyrazol-4-yl, naphth-1-yl, naphth-2-yl, 5-dimethylaminonaphth-1-yl, thien-2-yl, 4-methylphenylmethyl, 4-(1,1-dimethylpropyl)phenyl, 4-biphenyl, or quinolin-8-yl.

14. A compound as claimed in claim 1 or claim 2 wherein n is 1, V is HONH—, $R_1$ is $C_1$–$C_6$ alkyl, fluoro-substituted $C_1$–$C_{12}$ alkyl, or cycloalkyl($C_1$–$C_6$ alkyl), $R_2$ is piperidin-1-yl, and $R_3$ is hydrogen, acetyl or methyl.

15. A compound as claimed in claim 14 wherein $R_4$ is methyl, ethyl, n-butyl, n-octyl, dimethylamino, trifluoromethyl, phenyl, 4-methoxyphenyl, 4-butoxyphenyl, 2,5-dimethoxyphenyl, 4-chlorophenyl, 3,4-dichlorophenyl, 2-chloro-5-methoxyphenyl, 2-chloro-5-trifluoromethylphenyl, 5-chloro-1,3-dimethyl-phenyl-, 5-chloro-1,3-dimethyl-1H-pyrazol-4-yl, naphth-1-yl, naphth-2-yl, 5-dimethylaminonaphth-1-yl, thien-2-yl, 4-methylphenylmethyl, 4-(1,1-dimethylpropyl)phenyl, 4-biphenyl, or quinolin-8-yl.

16. A compound as claimed in claim 1 wherein
$R_1$ is a $C_1$–$C_{12}$ alkyl, $C_2$–$C_{12}$ alkenyl, $C_2$–$C_{12}$ alkynyl, phenyl($C_1$–$C_6$ alkyl)-, heteroaryl($C_1$–$C_6$ alkyl)-, non-aryl heterocyclyl($C_1$–$C_6$ alkyl)-, cycloalkyl($C_1$–$C_6$ alkyl)-, cycloalkenyl($C_1$–$C_6$ alkyl)-, phenoxy($C_1$–$C_6$ alkyl)-, heteroaryloxy($C_1$–$C_6$ alkyl)-, phenyl($C_1$–$C_6$ alkyl)O($C_1$–$C_6$ alkyl)-, heteroaryl($C_1$–$C_6$ alkyl)O ($C_1$–$C_6$ alkyl)-, phenyl($C_1$–$C_6$ alkyl)S($C_1$–$C_6$ alkyl)-or heteroaryl($C_1$–$C_6$ alkyl)S($C_1$–$C_6$ alkyl)- group, any one of which may be optionally substituted by $C_1$–$C_6$ alkyl, trifluoromethyl, $C_1$–$C_6$ alkoxy, halo, cyano (—CN), phenyl, substituted phenyl or heteroaryl; and
$R_4$ is optionally substituted $C_1$–$C_6$ alkyl, cycloalkyl, cycloalkenyl, di-($C_1$–$C_6$ alkyl)amino, heterocyclyl, phenyl, naphthyl, or heteroaryl;
or a pharmaceutically acceptable salt hydrate or solvate thereof.

17. A compound as claimed in claim 1 which is selected from the group consisting of
2S-{[(4-Methoxybenzenesulfonyl)-methyl-amino]-methyl}-5-methyl-3R-(piperidine-1-carbonyl)-hexanoic acid hydroxyamide,
5-Methyl-2S-{[methyl-(toluene-4-sulfonyl)-amino]-methyl]-3R-(piperidine-1-carbonyl)-hexanoic acid hydroxyamide,
2S-{[(5-Dimethylamino-naphthalene-1-sulfonyl)-methyl-amino]-methyl}-5-methyl-3R-(piperidine-1-carbonyl)-hexanoic acid hydroxyamide,
5-Methyl-2S-{[methyl-(naphthalene-2-sulfonyl)-amino]-methyl-3R-(piperidine-1-carbonyl)-hexanoic acid hydroxyamide,
5-Methyl-2S-[(methyl-phenylmethanesulfonyl-amino)-methyl]-3R-(piperidine-1-carbonyl)-hexanoic acid hydroxyamide,
2S-{[(4-Butoxybenzenesulfonyl)-methyl-amino]-methyl}-5-methyl-3R-(piperidine-1-carbonyl)-hexanoic acid hydroxyamide,
2S-{[(Biphenyl-4-sulfonyl)-methyl-amino}-methyl}-5-methyl-3R-(piperidine-1-carbonyl)-hexanoic acid hydroxyamide,
and pharmaceutically acceptable salts, hydrates and solvates thereof.

18. A compound which is a member of the group consisting of:
2S-{[(5-Dimethylaminonaphthalene-1-sulfonyl)-methyl-amino]-methyl}-5-methyl-3R-(morpholine-4-carbonyl)-hexanoic acid hydroxyamide
3R-Cyclopentylmethyl-N-hydroxy-2S-[(methanesulfonyl-methyl-amino)-methyl)]-4-oxo-4-piperidin-1-yl-butyramide
3R-Cyclopentylmethyl-N-hydroxy-2S-[(methanesulfonyl-methyl-amino)-methyl)]-4-morpholin-4-yl-4-oxo-butyramide
3R-Cyclopentylmethyl-N-hydroxy-2S-{[(4-benzenesulfonyl)-methyl-amino]-methyl}-4-oxo-4-piperidine-1-yl-butyramide
3R-Cyclopentylmethyl-N-hydroxy-2S-{[(4-benzenesulfonyl)-methyl-amino]-methyl}-4-morpholin-4-yl-4-oxo-butyramide
2S-[(Methanesulfonyl-methyl-amino)-methyl]-5-methyl-3R-(morpholine-4-carbonyl)-hexanoic acid hydroxyamide
2S-{[Ethyl-(4-methoxy-benzenesulfonyl)-amino]-methyl}-5-methyl-3R-(morpholine-4-carbonyl)-hexanoic acid hydroxyamide
2S-{[Ethyl-(4-methoxy-benzenesulfonyl)-amino]-methyl}-5-methyl-3R-(piperidine-1-carbonyl)-hexanoic acid hydroxyamide
3R-Cyclopentylmethyl-2S-{[ethyl-(4-methoxy-benzenesulfonyl)-amino]-methyl}-N-hydroxy-4-oxo-4-morpholine-1-yl-butyramide
3R-Cyclopentylmethyl-2S-{[ethyl-(4-methoxy-benzenesulfonyl)-amino]-methyl}-N-hydroxy-4-morpholine-4-yl-4-oxo-butyramide
3R-Cyclopentylmethyl-2S-{[(5-dimethyamino-naphthalene-1-sulfonyl)-methyl-amino]-methyl}-N-hydroxy-4-oxo-4-piperidine-1-yl-butyramide
3R-Cyclopentylmethyl-2S-{[(5-dimethyamino-naphthalene-1-sulfonyl)-methyl-amino]-methyl}-N-hydroxy-4-morpholine-4-yl-4-oxo-butyramide
2S-{[(5-Dimethylaminonaphthalene-1-sulfonyl)-ethyl-amino]-methyl}-5-methyl-3R-(morpholine-4-carbonyl)-hexanoic acid hydroxyamide
2S-{[(5-Dimethylaminonaphthalene-1-sulfonyl)-methyl-amino]-methyl}-5-methyl-3R-(piperidine-1-carbonyl)-hexanoic acid hydroxyamide
3R-Cyclopentylmethyl-2S-[(ethanesulfonyl-methyl-amino)-methyl]-N-hydroxy-4-oxo-4-piperidin-1-yl-butyramide
3R-Cyclopentylmethyl-N-hydroxy-2S-{[methyl-(propane-2-sulfonyl]-amino]-methyl}-4-oxo-4-piperidin-1-yl-butyramide
3R-Cyclopentylmethyl-N-hydroxy-2S-{[methyl-(octane-1-sulfonyl)-amino]-methyl}-4-oxo-4-piperidin-1-yl-butyramide
3R-Cyclopentylmethyl-N-hydroxy-2S-[(methyl-trifluoromethanesulfonyl-amino)-methyl]-4-oxo-4-piperidin-1-yl-butyramide
2S-{[(4-Chloro-benzenesulfonyl)-methyl-amino] methyl}-3R-cyclopentylmethyl-N-hydroxy-4-oxo-4-piperidin-1-yl-butyramide 3R-Cyclopentylmethyl-N-hydroxy-2S-{[methyl-(quinoline-8-sulfonyl)-amino]-methyl}-4-oxo-4-piperidin-1-yl-butyramide 3R-Cyclopentylmethyl-N-hydroxy-2S-{[methyl-(naphthalene-1-sulfonyl)-amino]-methyl}-4-oxo-4-piperidin-1-yl-butyramide 3R-Cyclopentylmethyl-N-hydroxy-2S-{[(isoquinoline-5-sulfonyl)-methyl- amino]-methyl}4-oxo-4-piperidin-1-yl-butyramide 3R-Cyclopentylmethyl-2S-{[(6-dimethylamino-naphthalene-1-sulfonyl)-methyl-amino]-methyl}-N-hydroxy-4-oxo-4-piperidin-1-yl-butyramide 3R-Cyclopentylmethyl-2S-{[dimethylsulfamoyl-methyl-amino]-methyl}-N-hydroxy-4-oxo-4-piperidin-1-yl-butyramide 2S-[(Butyl-methanesulfonyl-amino)-methyl]-3R-cyclopentylmethyl-N-hydroxy-4-oxo-4-piperidin-1-yl-butyramide 3R-Cyclopentylmethyl-N-hydroxy-2S-[(isopropyl-methanesulfonyl)-amino)-methyl]-4-oxo-4-piperidin-1-yl-butyramide 2S-[(tert-Butyl-methanesulfonyl)-amino)-methyl]-3R-cyclopentylmethyl-N-hydroxy-4-oxo-4-piperidin-1-yl-butyramide 3R-Cyclopentylmethyl-N-hydroxy-2S-[(cyclopropyl-methanesulfonyl)-amino)-methyl]-4-oxo-4-piperidin-1-yl-butyramide 2S-[(Cyclopentyl-methanesulfonyl)-amino)-methyl]-3R-cyclopentylmethyl-N-hydroxy-4-oxo-4-piperidin-1-yl-butyramide and pharmaceutically acceptable salts hydrates and solvates thereof.

19. A pharmaceutical or veterinary composition comprising a compound as claimed in claim 1 or a pharmaceutically or veterinarily acceptable salt, hydrate or solvate thereof, together with a pharmaceutically or veterinarily acceptable excipient or carrier.

20. A method of treating a disease or condition mediated by collagenase, which method comprises administering to the mammal in need thereof an inhibiting amount of collagenase inhibiting amount of a compound as claimed in claim 1.

21. A method as claimed in claim 20, wherein the mammal suffers from a disease or condition selected from a group consisting of rheumatoid arthritis, osteoarthritis, periodontitis, gingivitis, corneal ulceration, tumor invasion by secondary metastasis and a neuroinflammatory disorder.

22. A compound as claimed in claim 7 wherein $R_2$ is selected from the group consisting of piperidin-1-yl, 2-(methylcarbamoyl)-1-pyrrolidinyl, 2-(hydroxymethyl)-1-pyrrolidinyl, 4-hydroxypiperidino, 2-(methylcarbamoyl)piperidino, 4-hydroxyiminopiperidino, 4-methoxypiperidino, 4-methyl-1-piperazinyl, 4-phenyl-1-piperazinyl, 1,4-dioxa-8-azaspirodecan-8-yl, hexahydro-3-(methylcarbamoyl)-2-pyridazinyl, hexahydro-1-(benzyloxycarbonyl)-2-pyridazinyl, 5,5-dimethyl-4-methylcarbamoyl-thiazolidin-3-yl, or 5,5-dimethyl-4-propylcarbamoyl-thiazolidin-3-yl.

* * * * *